(12) United States Patent
Moinet et al.

(10) Patent No.: US 9,545,387 B2
(45) Date of Patent: Jan. 17, 2017

(54) COMPOSITION AND KIT COMPRISING PIPERAZINE DERIVATIVES AND METFORMIN, AND USE THEREOF IN THE TREATMENT OF DIABETES

(71) Applicant: METABOLYS, Lyons (FR)

(72) Inventors: Gérard Moinet, Orsay (FR); Gabriel Baverel, Saint Cyr au Mont d'Or (FR)

(73) Assignee: METABOLYS, Lyons (FR)

(*) Notice: Subject to any disclaimer, the term of this patent is extended or adjusted under 35 U.S.C. 154(b) by 0 days.

(21) Appl. No.: 14/651,755

(22) PCT Filed: Dec. 17, 2013

(86) PCT No.: PCT/EP2013/076987
§ 371 (c)(1),
(2) Date: Jun. 12, 2015

(87) PCT Pub. No.: WO2014/095929
PCT Pub. Date: Jun. 26, 2014

(65) Prior Publication Data
US 2015/0297539 A1    Oct. 22, 2015

(30) Foreign Application Priority Data
Dec. 17, 2012 (FR) .................. 12 62136

(51) Int. Cl.
| | | |
|---|---|---|
| *A61K 31/495* | (2006.01) | |
| *A61K 31/496* | (2006.01) | |
| *C07D 241/04* | (2006.01) | |
| *A61K 31/155* | (2006.01) | |
| *G01N 33/50* | (2006.01) | |
| *G01N 33/66* | (2006.01) | |

(52) U.S. Cl.
CPC .......... *A61K 31/155* (2013.01); *A61K 31/495* (2013.01); *A61K 31/496* (2013.01); *G01N 33/5041* (2013.01); *G01N 33/5067* (2013.01); *G01N 33/66* (2013.01); *C07D 241/04* (2013.01); *G01N 2333/62* (2013.01); *G01N 2500/02* (2013.01); *G01N 2500/10* (2013.01)

(58) Field of Classification Search
CPC .. A61K 31/495; A61K 31/496; A61K 31/497; C07D 241/04; C07D 295/182; C07D 295/192; C07D 295/205; C07D 295/26
See application file for complete search history.

(56) References Cited

U.S. PATENT DOCUMENTS

| | | |
|---|---|---|
| 6,376,495 B1 | 4/2002 | Moinet et al. |
| 2004/0236100 A1 | 11/2004 | Sharma et al. |
| 2012/0219623 A1 | 8/2012 | Meinicke |
| 2014/0155409 A1 | 6/2014 | Moinet et al. |
| 2014/0235650 A1 | 8/2014 | Moinet et al. |

FOREIGN PATENT DOCUMENTS

DK    WO 2005009976 A1 *  2/2005  .......... C07D 237/20

OTHER PUBLICATIONS

International Search Report for PCT/EP2013/076987 dated Feb. 13, 2014.
French Search Report for FR 1262136 dated Aug. 28, 2013.

* cited by examiner

*Primary Examiner* — Kamal Saeed
*Assistant Examiner* — Janet L Coppins
(74) *Attorney, Agent, or Firm* — B. Aaron Schulman, Esq.; Stites & Harbison, PLLC.

(57) ABSTRACT

The present disclosure relates to a composition including, in combination, metformin or a salt thereof, a pharmaceutically acceptable carrier or excipient and at least one compound of formula (I), or the enantiomers, diastereoisomers or pharmaceutically acceptable salts thereof. Formula (I) is as follows:

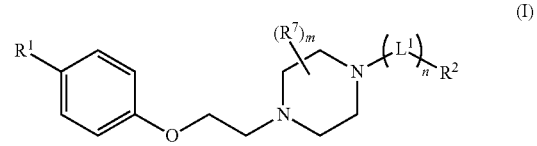

The present disclosure also relates to the use of this composition for the treatment of diseases associated with insulin resistance syndrome.

20 Claims, No Drawings

COMPOSITION AND KIT COMPRISING PIPERAZINE DERIVATIVES AND METFORMIN, AND USE THEREOF IN THE TREATMENT OF DIABETES

The present invention pertains to compositions and a kit comprising in association at least one derivative of piperazine or the pharmaceutically salts thereof and metformin or the pharmaceutically acceptable salts thereof, and to their uses in particular in the treatment of pathologies associated with insulin-resistance syndrome (or syndrome X) particularly in the treatment of Type 2 diabetes.

In recent years a major increase has been observed in the number of cases of diabetes across the world. In 2011, there were around 366 million diabetics in the world and the prediction for 2030 is in the order of over 550 million diabetics. Type 2 diabetes (destruction of insulin-producing cells) is chiefly treated with injection of insulin. Type 2 diabetes which is the most widespread (90% of diabetes cases) is characterized by tissue resistance to insulin and requires special treatment.

Numerous compounds have been proposed for the treatment of diabetes, and in particular of Type 2 diabetes. In particular, from document derivatives of piperazine are known. Also phenyl derivatives are known from WO02/100341.

At the current time, in about 40% of cases, treatment is not effective and the desired fasting glycaemia threshold of 1.26 g/liter of blood is not reached.

In addition, more than 40% of treated patients have a glycosylated haemoglobin level (HbA1c) higher than 7%, in particular after a treatment time of several years.

There is therefore a need for novel associations allowing more efficient treatment of pathologies associated with insulin-resistance syndrome and which limits phenomena of resistance to active ingredients.

It is therefore one objective of the invention to provide efficient compositions and associations for the treatment of pathologies associated with insulin-resistance syndrome. Another objective of the present invention is to propose compositions and associations allowing the inhibition of neoglucogenesis in particular.

A further objective of the present invention is to provide means for treating pathologies associated with insulin-resistance syndrome, and in particular Type 2 diabetes.

Other objectives will become apparent on reading the following description of the invention.

These objectives are met with the present invention which proposes a composition comprising in association metformin or a metformin salt and at least one compound of formula (I) and the enantiomers, diastereoisomers and pharmaceutically acceptable salts thereof:

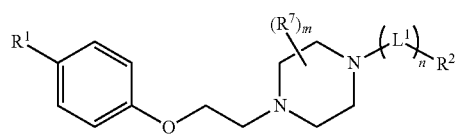

(I)

where:
$R^1$ is a group from among:
—C(O)C$R^3R^4$C$R^5R^6$C(O)OH;
—C(OH)(H)C$R^3R^4$C$R^5R^6$C(O)OH;
—(CH$_2$)$_4$C(O)OH; or

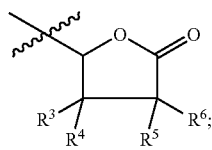

m is an integer ranging from 0 to 8;
n is 0 or 1;
$L^1$ is a group from among —C(O)—, —C(O)O— or —S(O)$_2$—;
$R^2$ is:
5-, 6- or 7-membered carbocycle group, saturated, partly unsaturated or aromatic, substituted or unsubstituted;
8- to 14-membered polycarbocycle group, preferably 9 or 10-membered, saturated, partly unsaturated or aromatic, substituted or unsubstituted;
5-, 6- or 7-membered heterocycle group, substituted or unsubstituted, saturated, partly unsaturated or aromatic possibly having 1, 2 or 3 heteroatoms, the same or different selected in particular from among nitrogen, oxygen or sulfur;
8- to 14-membered polyheterocycle group, preferably 9- or 10-membered, substituted or unsubstituted, saturated, partly unsaturated or aromatic possibly having 1, 2 or 3 heteroatoms, the same or different, selected in particular from among nitrogen, oxygen or sulfur;
-$L^2$-carbocycle group, the carbocycle being 5-, 6- or 7-membered, saturated, partly unsaturated or aromatic, substituted or unsubstituted;
-$L^2$-polycarbocycle group, the polycarbocycle being 8- to 14-membered, preferably 9- or 10-membered, saturated, partly unsaturated or aromatic, substituted or unsubstituted;
-$L^2$-heterocycle group, the heterocycle being 5-, 6- or 7-membered, substituted or unsubstituted, saturated, partly unsaturated or aromatic and possibly having 1, 2 or 3 heteroatoms, the same or different, selected in particular from among nitrogen, oxygen or sulfur;
-$L^2$-polyheterocycle group, the polyheterocycle being 8- to 14-membered, preferably 9- or 10-membered, substituted or unsubstituted, saturated partly unsaturated or aromatic possibly having 1, 2 or 3 heteroatoms, the same or different, selected in particular from among nitrogen, oxygen or sulfur; or
hydrocarbon group, straight-chain or branched, $C_1$ to $C_5$, preferably $C_1$ to $C_4$, preferably alkyl, straight-chain or branched, $C_1$ to $C_5$, preferably $C_1$ to $C_4$;
$L^2$ representing an alkyl, straight-chain or branched, $C_1$ to $C_5$, preferably $C_1$ to $C_4$;
$R^3$, $R^4$, $R^5$ and $R^6$, the same or different, are:
a hydrogen atom;
an alkyl group, straight-chain or branched, $C_1$ to $C_5$, preferably $C_1$ to $C_4$;
5-, 6- or 7-membered carbocycle group, saturated, partly unsaturated or aromatic, substituted or unsubstituted; or
$R_3$ and $R_4$, together with the carbon atom to which they are attached, form a 5-, 6- or 7-membered carbocycle, substituted or unsubstituted, preferably saturated; e.g. cyclopentyl, cyclohexyl; or
$R_5$ and $R_6$, together with the carbon atom to which they are attached, form a 5-, 6- or 7-membered carbocycle, substituted or unsubstituted, preferably saturated; e.g. cyclopentyl, cyclohexyl;
$R^7$, the same or different, are:

an alkyl, straight-chain or branched, $C_1$ to $C_5$, preferably $C_1$ to $C_4$; e.g. methyl, ethyl, propyl, iso-propyl, butyl, ter-butyl;

-$L^2$-carbocycle group, the carbocycle being 5-, 6- or 7-membered, saturated, partly unsaturated or aromatic, substituted or unsubstituted;

-$L^2$-polycarbocycle group, the polycarbocycle being 8- to 14-membered, preferably 9- or 10-membered, saturated partly unsaturated or aromatic substituted or unsubstituted;

-$L^2$-heterocycle group, the heterocycle being 5-, 6- or 7-membered, substituted or unsubstituted, saturated, partly unsaturated or aromatic, and possibly having 1, 2 or 3 heteroatoms, the same or different, selected in particular from among nitrogen, oxygen or sulfur; or -$L^2$-polyheterocycle group, the polyheterocycle being 8- to 14-membered, preferably 9- or 10-membered, substituted or unsubstituted, saturated, partly unsaturated or aromatic and possibly having 1, 2 or 3 heteroatoms, the same or different, selected in particular from among nitrogen, oxygen or sulfur.

The carbocycles, polycarbocycles, heterocycles and polyheterocycles are unsubstituted or substituted by one or more substituents, the same or different, selected in particular from among:

$C_1$ to $C_6$ alkoxy group, straight-chain or branched, e.g. methoxy, ethoxy, propoxy, iso-propoxy, butoxy, ter-butoxy;

a halogen atom;

a hydrocarbon group, straight-chain or branched, preferably alkyl, $C_1$ to $C_5$, preferably $C_1$ to $C_4$, e.g. methyl, ethyl, propyl, butyl, iso-propyl, ter-butyl;

a hydrocarbon group, straight-chain or branched, preferably alkyl, $C_1$ to $C_5$, preferably $C_1$ to $C_4$, substituted in particular by one more halogen atoms;

a cyano group (—CN);

an alkyl sulfonyl group (—S(O)$_2$-alkyl) wherein the alkyl is straight-chain or branched, $C_1$ to $C_5$, preferably $C_1$ to $C_4$, e.g. methyl, ethyl, propyl, butyl, iso-propyl, ter-butyl; or 5, 6 or 7-membered carbocycle group, saturated, partly unsaturated or aromatic, preferably phenyl, unsubstituted or substituted in particular by one or more substituents, the same or different, selected in particular from among a halogen atom, $C_1$ to $C_6$ alkoxy group, straight-chain or branched e.g. methoxy, ethoxy, propoxy, iso-propoxy, butoxy, ter-butoxy; $C_1$ to $C_5$ alkyl group preferably $C_1$ to $C_4$, e.g. methyl, ethyl, propyl, butyl, iso-propyl, ter-butyl.

Preferably, in the formula (I) compound, $R^7$, the same or different, are:

$C_1$ to $C_3$ alkyl, straight-chain or branched, or

-$L^2$-carbocycle group, $L^2$ being an alkyl, straight-chain or branched, $C_1$ to $C_5$, preferably $C_1$ to $C_4$; and the carbocycle being aromatic with 5 or 6 members, e.g. phenyl, optionally substituted.

Preferably in the formula (I) compound, m is 0 or 1, preferably 0.

Preferably, in the formula (I) compound, $R^2$ is:

a 6-membered aromatic carbocyle group, unsubstituted or substituted by one or more substituents, the same or different, selected in particular from among:

$C_1$ to $C_6$ alkoxy group, preferably $C_1$ to $C_3$, straight-chain or branched, e.g. methoxy, ethoxy, propoxy, iso-propoxy, butoxy, ter-butoxy;

a halogen atom, e.g. fluorine, chlorine, bromine;

$C_1$ to $C_5$ alkyl group, preferably $C_1$ to $C_4$, straight-chain or branched e.g. methyl, ethyl, propyl, butyl, iso-propyl, ter-butyl;

$C_1$ à $C_5$ alkyl group, preferably $C_1$ to $C_4$, straight-chain or branched, substituted in particular by one or more halogen atoms e.g. trifluoromethyl;

cyano group (—CN);

alkylsulfonyl group (—S(O)$_2$-alkyl) wherein the alkyl is straight-chain or branched, $C_1$ to $C_5$, preferably $C_1$ to $C_4$, e.g. methyl, ethyl, propyl, butyl, iso-propyl, ter-butyl e.g. methane sulfonyl (—S(O)$_2$CH$_3$); or aryl group, preferably phenyl, unsubstituted or substituted in particular by one or more substituents, the same or different, selected in particular from among a halogen atom, $C_1$ to $C_6$ alkoxy group, straight-chain or branched e.g. methoxy, ethoxy, propoxy, iso-propoxy, butoxy, ter-butoxy; a $C_1$ to $C_5$ alkyl group, preferably $C_1$ to $C_4$, e.g. methyl, ethyl, propyl, butyl, iso-propyl, ter-butyl;

an aromatic heterocycle group with 5 or 6 members, having 1, 2 or 3 heteroatoms, the same or different, selected in particular from among nitrogen, sulfur and oxygen, unsubstituted or substituted by one or more substituents, the same or different selected in particular from among:

$C_1$ to $C_6$ alkoxy group, preferably $C_1$ to $C_3$, straight-chain or branched e.g. methoxy, ethoxy, propoxy, iso-propoxy, butoxy, ter-butoxy;

a halogen atom e.g. fluorine, chlorine, bromine;

$C_1$ to $C_5$ alkyl group, preferably $C_1$ to $C_4$, straight-chain or branched e.g. methyl, ethyl, propyl, butyl, iso-propyl, ter-butyl;

$C_1$ to $C_5$ alkyl group, preferably $C_1$ to $C_4$, straight-chain or branched, substituted in particular by one or more halogen atoms e.g. trifluoromethyl;

cyano group (—CN);

an alkylsulfonyl group (—S(O)$_2$-alkyl) wherein the alkyl is straight-chain or branched, $C_1$ to $C_5$, preferably $C_1$ to $C_4$ e.g. methyl, ethyl, propyl, butyl, iso-propyl, ter-butyl e.g. methane sulfonyl (—S(O)$_2$CH$_3$); or an aryl group, preferably phenyl, unsubstituted or substituted in particular by one or more substituents, the same or different, selected in particular from among a halogen atom, $C_1$ to $C_6$ alkoxy group, straight-chain or branched e.g. methoxy, ethoxy, propoxy, iso-propoxy, butoxy, ter-butoxy; $C_1$ to $C_5$ alkyl group preferably $C_1$ to $C_4$ e.g. methyl, ethyl, propyl, butyl, iso-propyl, ter-butyl;

preferably the heterocycle is unsubstituted or substituted by a phenyl group unsubstituted or substituted in particular by one or more substituents, the same or different, selected in particular from among a halogen atom, $C_1$ to $C_6$ alkoxy group, straight-chain or branched e.g. methoxy, ethoxy, propoxy, iso-propoxy, butoxy, ter-butoxy; $C_1$ to $C_5$ alkyl group, preferably $C_1$ to $C_4$, e.g. methyl, ethyl, propyl, butyl, iso-propyl, ter-butyl;

8- to 14-membered aromatic polyheterocycle, preferably 9- or 10-membered, having 1, 2 or 3 heteroatoms, the same or different, selected from among nitrogen, sulfur and oxygen, unsubstituted or substituted by one or more substituents, the same or different, selected in particular from among:

$C_1$ to $C_6$ alkoxy group, preferably $C_1$ to $C_3$, straight-chain or branched e.g. methoxy, ethoxy, propoxy, iso-propoxy, butoxy, ter-butoxy;

a halogen atom e.g. fluorine, chlorine, bromine;

$C_1$ to $C_5$ alkyl group, preferably $C_1$ to $C_4$, straight-chain or branched e.g. methyl, ethyl, propyl, butyl, iso-propyl, ter-butyl;

$C_1$ to $C_5$ alkyl group, preferably $C_1$ to $C_4$, straight-chain or branched, substituted in particular by one or more halogen atoms e.g. trifluoromethyl;

a cyano group (—CN);

an alkylsulfonyl group (—S(O)$_2$-alkyl) wherein the alkyl is straight-chain or branched, $C_1$ to $C_5$, preferably $C_1$ to $C_4$, e.g. methyl, ethyl, propyl, butyl, iso-propyl, ter-butyl, e.g. methane sulfonyl (—S(O)$_2$CH$_3$); or an aryl group, preferably phenyl, unsubstituted or substituted in particular by one or more substituents, the same or different, selected in particular from among a halogen atom, $C_1$ to $C_6$ alkoxy group, straight-chain or branched e.g. methoxy, ethoxy, propoxy, iso-propoxy, butoxy, ter-butoxy; $C_1$ to $C_5$ alkyl group, preferably $C_1$ to $C_4$, e.g. methyl, ethyl, propyl, butyl, iso-propyl, ter-butyl;

an alkyl group, straight-chain or branched, $C_1$ to $C_5$, preferably $C_1$ to $C_4$, e.g. methyl, ethyl, propyl, butyl, iso-propyl, ter-butyl; or -$L^2$-carbocycle group, the carbocycle being aromatic with 5 or 6 members, e.g. phenyl, unsubstituted or substituted by one or more substituents, the same or different, selected in particular from among:

$C_1$ to $C_6$ alkoxy group, preferably $C_1$ to $C_3$, straight-chain or branched e.g. methoxy, ethoxy, propoxy, iso-propoxy, butoxy, ter-butoxy;

a halogen atom e.g. fluorine, chlorine, bromine;

$C_1$ to $C_5$ alkyl group, preferably $C_1$ to $C_4$, straight-chain or branched e.g. methyl, ethyl, propyl, butyl, iso-propyl, ter-butyl;

$C_1$ to $C_5$, alkyl group, preferably $C_1$ to $C_4$, straight-chain or branched, substituted in particular by one or more halogen atoms e.g. trifluoromethyl;

a cyano group (—CN);

an alkylsulfonyl group (—S(O)$_2$-alkyl) wherein the alkyl is straight-chain or branched, $C_1$ to $C_5$, preferably $C_1$ to $C_4$, e.g. methyl, ethyl, propyl, butyl, iso-propyl, ter-butyl, e.g. methane sulfonyl (—S(O)$_2$CH$_3$); or an aryl group, preferably phenyl, unsubstituted or substituted in particular by one or more substituents, the same or different, selected in particular from among a halogen atom, $C_1$ to $C_6$ alkoxy group, straight-chain or branched e.g. methoxy, ethoxy, propoxy, iso-propoxy, butoxy, ter-butoxy; $C_1$ to $C_5$ alkyl group, preferably $C_1$ to $C_4$, e.g. methyl, ethyl, propyl, butyl, iso-propyl, ter-butyl;

$L^2$ being an alkyl group, straight-chain or branched, $C_1$ to $C_5$, preferably $C_1$ to $C_4$, e.g. methyl, ethyl, propyl, butyl, iso-propyl, ter-butyl.

Preferably, in the formula (I) compound, $R^2$ is:

a phenyl, unsubstituted or substituted by one or more substituents, the same or different, selected in particular from among:

$C_1$ to $C_6$ alkoxy group, preferably $C_1$ to $C_3$, straight-chain or branched e.g. methoxy, ethoxy, propoxy, iso-propoxy, butoxy, ter-butoxy;

a halogen atom e.g. fluorine, chlorine, bromine;

$C_1$ à $C_5$ alkyl group, preferably $C_1$ to $C_4$, straight-chain or branched e.g. methyl, ethyl, propyl, butyl, iso-propyl, ter-butyl;

$C_1$ to $C_5$ alkyl group, preferably $C_1$ to $C_4$, straight-chain or branched, substituted in particular by one or more halogen atoms e.g. trifluoromethyl;

a cyano group (—CN);

an alkylsulfonyl group (—S(O)$_2$-alkyl) wherein the alkyl is straight-chain or branched, $C_1$ to $C_5$, preferably $C_1$ to $C_4$, e.g. methyl, ethyl, propyl, butyl, iso-propyl, ter-butyl, e.g. methane sulfonyl (—S(O)$_2$CH$_3$); or a phenyl group, unsubstituted or substituted in particular by one or more substituents, the same or different, selected in particular from among a halogen atom, $C_1$ to $C_6$ alkoxy group, straight-chain or branched, e.g. methoxy, ethoxy, propoxy, iso-propoxy, butoxy, ter-butoxy; $C_1$ to $C_5$ alkyl group, preferably $C_1$ to $C_4$, e.g. methyl, ethyl, propyl, butyl, iso-propyl, ter-butyl;

preferably the substituent(s) are at ortho or para position on the phenyl;

a monocyclic or polycyclic heteroaryl selected from among

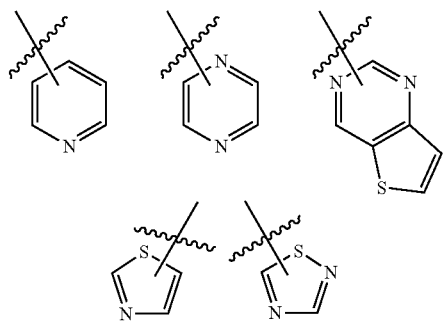

unsubstituted or substituted by one or more substituents, the same or different, selected in particular from among:

$C_1$ to $C_6$ alkoxy group, preferably $C_1$ to $C_3$, straight-chain or branched, e.g. methoxy, ethoxy, propoxy, iso-propoxy, butoxy, ter-butoxy;

a halogen atom e.g. fluorine, chlorine, bromine;

$C_1$ to $C_5$ alkyl group, preferably $C_1$ to $C_4$, straight-chain or branched e.g. methyl, ethyl, propyl, butyl, iso-propyl, ter-butyl;

$C_1$ to $C_5$ alkyl group, preferably $C_1$ to $C_4$, straight-chain or branched, substituted in particular by one or more halogen atoms e.g. trifluoromethyl;

a cyano group (—CN);

an alkylsulfonyl group (—S(O)$_2$-alkyl) wherein the alkyl is straight-chain or branched, $C_1$ to $C_5$, preferably $C_1$ to $C_4$, e.g. methyl, ethyl, propyl, butyl, iso-propyl, ter-butyl e.g. methane sulfonyl (—S(O)$_2$CH$_3$); or a pheny group, unsubstituted or substituted in particular by one or more substituents, the same or different, selected in particular from among a halogen atom, $C_1$ to $C_6$ alkoxy group, straight-chain or branched e.g. methoxy, ethoxy, propoxy, iso-propoxy, butoxy, ter-butoxy; $C_1$ to $C_5$ alkyl group, preferably $C_1$ to $C_4$, e.g. methyl, ethyl, propyl, butyl, iso-propyl, ter-butyl;

preferably the mono or polycyclic heteroaryl is selected from among:

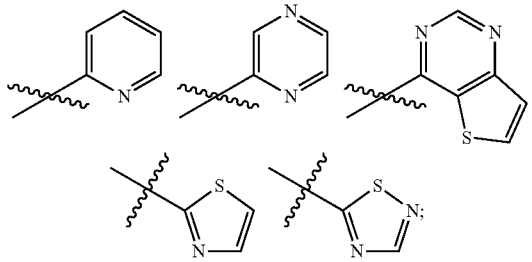

-L²-carbocycle group, the carbocycle being a phenyl unsubstituted or substituted by one or more substituents, the same or different, selected in particular from among:
  $C_1$ to $C_6$ alkoxy group, preferably $C_1$ to $C_3$, straight-chain or branched e.g. methoxy, ethoxy, propoxy, iso-propoxy, butoxy, ter-butoxy;
  a halogen atom e.g. fluorine, chlorine, bromine;
  $C_1$ to $C_5$ alkyl group, preferably $C_1$ to $C_4$, straight-chain or branched e.g. methyl, ethyl, propyl, butyl, iso-propyl, ter-butyl;
  $C_1$ to $C_5$ alkyl group, preferably $C_1$ to $C_4$, straight-chain or branched, substituted in particular by one or more halogen atoms e.g. trifluoromethyl;
  a cyano group (—CN);
  an alkylsulfonyl group (—S(O)₂-alkyl) wherein the alkyl is straight-chain or branched, $C_1$ to $C_5$, de preferably $C_1$ to $C_4$ e.g. methyl, ethyl, propyl, butyl, iso-propyl, ter-butyl, e.g. methane sulfonyl (—S(O)₂CH₃); or
  a phenyl group, unsubstituted or substituted in particular by one or more substituents, the same or different, selected in particular from among a halogen atom, $C_1$ to $C_6$ alkoxy group, straight-chain or branched e.g. methoxy, ethoxy, propoxy, iso-propoxy, butoxy, ter-butoxy; $C_1$ to $C_5$ alkyl group, preferably $C_1$ to $C_4$, e.g. methyl, ethyl, propyl, butyl, iso-propyl, ter-butyl;

L² representing an alkyl, straight-chain or branched, $C_1$ to $C_5$, preferably $C_1$ to $C_4$, preferably methyl, ethyl, propyl, butyl, iso-propyl, butyl, ter-butyl e.g. —CH₂—; or
  an alkyl group, straight-chain or branched, $C_1$ to $C_5$, preferably $C_1$ to $C_4$, e.g. methyl, ethyl, propyl, butyl, iso-propyl, ter-butyl.

Preferably in the formula (I) compound, R² is:
a phenyl, unsubstituted or substituted by one or more substituents, the same or different, selected in particular from among:
  $C_1$ to $C_6$ alkoxy group, preferably $C_1$ to $C_3$, straight-chain or branched e.g. methoxy, ethoxy, propoxy, iso-propoxy, butoxy, ter-butoxy;
  a halogen atom e.g. fluorine, chlorine, bromine;
  $C_1$ to $C_5$ alkyl group, preferably $C_1$ to $C_4$, straight-chain or branched e.g. methyl, ethyl, propyl, butyl, iso-propyl, ter-butyl;
  $C_1$ to $C_5$ alkyl group preferably $C_1$ to $C_4$, straight-chain or branched, substituted in particular by one or more halogen atoms e.g. trifluoromethyl;
  a cyano group (—CN); or
  an alkylsulfonyl group (—S(O)₂-alkyl) wherein the alkyl is straight-chain or branched, $C_1$ to $C_5$, preferably $C_1$ to $C_4$, e.g. methyl, ethyl, propyl, butyl, iso-propyl, ter-butyl, e.g. methane sulfonyl (—S(O)₂CH₃);
  preferably the substituent(s) are at ortho or para position on the phenyl;
a monocylic or polycyclic heteroaryl selected from among:

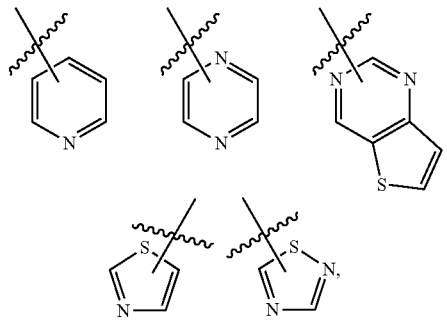

unsubstituted or substituted by one or more substituents, the same or different, selected in particular from among:
  $C_1$ to $C_6$ alkoxy group, preferably $C_1$ to $C_3$, straight-chain or branched e.g. methoxy, ethoxy, propoxy, iso-propoxy, butoxy, ter-butoxy;
  a halogen atom e.g. fluorine, chlorine, bromine;
  $C_1$ to $C_5$ alkyl group, preferably $C_1$ to $C_4$, straight-chain or branched e.g. methyl, ethyl, propyl, butyl, iso-propyl, ter-butyl;
  $C_1$ to $C_5$ alkyl group, preferably $C_1$ to $C_4$, straight-chain or branched, substituted in particular by one or more halogen atoms e.g. trifluoromethyl;
  a cyano group (—CN);
  an alkylsulfonyl group (—S(O)₂-alkyl) wherein the alkyl is straight-chain or branched, $C_1$ to $C_5$, preferably $C_1$ to $C_4$ e.g. methyl, ethyl, propyl, butyl, iso-propyl, ter-butyl, e.g. methane sulfonyl (—S(O)₂CH₃); or
  a phenyl group, unsubstituted or substituted in particular by one or more substituents, the same or different, selected in particular from among a halogen atom, $C_1$ to $C_6$ alkoxy group e.g. methoxy, ethoxy, propoxy, iso-propoxy, butoxy, ter-butoxy; $C_1$ to $C_5$ alkyl group, preferably $C_1$ to $C_4$ e.g. methyl, ethyl, propyl, butyl, iso-propyl, ter-butyl;

preferably the mono or polycyclic heteroaryl is selected from among:

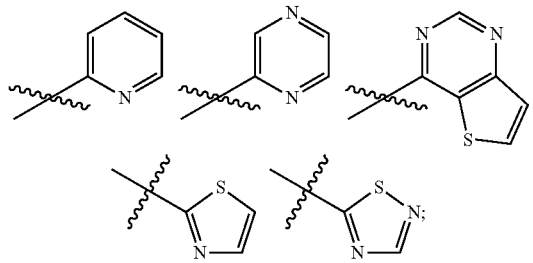

-L²-carbocycle group, the carbocycle being a phenyl, unsubstituted or substituted by one or more substituents, the same or different, selected in particular from among:

$C_1$ to $C_6$ alkoxy group, preferably $C_1$ to $C_3$, straight-chain or branched e.g. methoxy, ethoxy, propoxy, iso-propoxy, butoxy, ter-butoxy;

a halogen atom e.g. fluorine, chlorine, bromine;

$C_1$ to $C_5$ alkyl group, preferably $C_1$ to $C_4$, straight-chain or branched e.g. methyl, ethyl, propyl, butyl, iso-propyl, ter-butyl;

$C_1$ to $C_5$ alkyl group, preferably $C_1$ to $C_4$, straight-chain or branched, substituted in particular by one or more halogen atoms e.g. trifluoromethyl;

a cyano group (—CN); or an alkylsulfonyl group (—S(O)$_2$-alkyl) wherein the alkyl is straight-chain or branched, $C_1$ to $C_5$, preferably $C_1$ to $C_4$ e.g. methyl, ethyl, propyl, butyl, iso-propyl, ter-butyl, e.g. methane sulfonyl (—S(O)$_2$CH$_3$);

$L^2$ representing an alkyl, straight-chain or branched, $C_1$ to $C_5$, preferably $C_1$ to $C_4$, preferably methyl, ethyl, propyl, butyl, iso-propyl, butyl, ter-butyl e.g. —CH$_2$—; or an alkyl group, straight-chain or branched, $C_1$ to $C_5$, preferably $C_1$ to $C_4$ e.g. methyl, ethyl, propyl, butyl, iso-propyl, ter-butyl.

Preferably, in the formula (I) compound, $R^2$ is:

a 6-membered aromatic carbocycle group, preferably phenyl unsubstituted or substituted by one or more substituents, the same or different, selected in particular from among:

$C_1$ to $C_6$ alkoxy group, preferably $C_1$ to $C_3$, straight-chain or branched e.g. methoxy, ethoxy, propoxy, iso-propoxy, butoxy, ter-butoxy;

a halogen atom e.g. fluorine, chlorine, bromine;

$C_1$ to $C_5$ alkyl group, preferably $C_1$ to $C_4$, straight-chain or branched e.g. methyl, ethyl, propyl, butyl, iso-propyl, ter-butyl;

$C_1$ to $C_5$ alkyl group, preferably $C_1$ to $C_4$, straight-chain or branched substituted in particular by one or more halogen atoms e.g. trifluoromethyl;

an aromatic heterocycle group with 5 or 6 members, having 1, 2 or 3 heteroatoms, the same or different, selected in particular from among nitrogen, sulfur and oxygen, preferably pyridine unsubstituted or substituted by one or more substituents, the same or different, selected in particular from among:

$C_1$ to $C_6$ alkoxy group, preferably $C_1$ to $C_3$, straight-chain or branched e.g. methoxy, ethoxy, propoxy, iso-propoxy, butoxy, ter-butoxy;

a halogen atom e.g. fluorine, chlorine, bromine;

$C_1$ to $C_5$ alkyl group, preferably $C_1$ to $C_4$, straight-chain or branched e.g. methyl, ethyl, propyl, butyl, iso-propyl, ter-butyl;

$C_1$ to $C_5$ alkyl group, preferably $C_1$ to $C_4$, straight-chain or branched, substituted in particular by one or more halogen atoms e.g. trifluoromethyl.

Preferably in the formula (I) compound, $R^2$ is:

a phenyl group unsubstituted or substituted by one or more substituents, the same or different, selected in particular from among:

$C_1$ to $C_6$ alkoxy group, preferably $C_1$ to $C_3$, straight-chain or branched e.g. methoxy, ethoxy, propoxy, iso-propoxy, butoxy, ter-butoxy;

a halogen atom e.g. fluorine, chlorine, bromine;

a pyridine group.

Preferably, in the formula (I) compound, $R^3$, $R^4$, $R^5$ and $R^6$, the same or different, are:

a hydrogen atom;

an alkyl group, straight-chain or branched, $C_1$ to $C_5$, preferably $C_1$ to $C_4$, e.g. methyl, ethyl, propyl, butyl, iso-propyl, ter-butyl;

5-, 6- or 7-member carbocycle, saturated, partly unsaturated or aromatic, preferably saturated e.g. cyclopentyl, cyclohexyl, substituted or unsubstituted; or $R_3$ and $R_4$, together with the carbon atom to which they are attached, form a 5-, 6- or 7-membered carbocycle, substituted or unsubstituted, preferably saturated; e.g. cyclopentyl, cyclohexyl; or $R_5$ and $R_6$, together with the carbon atom to which they are attached, form a 5-, 6- or 7-membered carbocycle, substituted or unsubstituted, preferably saturated; e.g. cyclopentyl, cyclohexyl.

Preferably, in the formula (I) compound $R^3$, $R^4$ each represent a hydrogen atom and $R^5$ and $R^6$, the same or different, represent:

a hydrogen atom;

an alkyl group, straight-chain or branched, $C_1$ to $C_5$, preferably $C_1$ to $C_4$, e.g. methyl, ethyl, propyl, butyl, iso-propyl, ter-butyl;

5-, 6- or 7-membered carbocycle, saturated, partly unsaturated or aromatic, preferably saturated, e.g. cyclopentyl, cyclohexyl, substituted or unsubstituted; or $R_3$ and $R_4$, together with the carbon atom to which they are attached, form a 5-, 6- or 7-membered carbocycle, substituted or unsubstituted, preferably saturated; e.g. cyclopentyl, cyclohexyl; or $R_5$ and $R_6$, together with the carbon atom to which they are attached, form a 5-, 6- or 7-membered carbocycle, substituted or unsubstituted, preferably saturated; e.g. cyclopentyl, cyclohexyl.

Preferably in the formula (I) compound $R^3$, $R^4$, $R^5$ and $R^6$ each represent a hydrogen atom.

Preferably in the formula (I) compound n is 0.

In one particular embodiment, in the formula (I) compounds $R^1$ represents a group from among —C(O)CR$^3$R$^4$CR$^5$R$^6$C(O)OH or —(CH$_2$)$_4$C(O)OH, m, n, $L^1$, $R^2$, $L^2$, $R^3$, $R^4$, $R^5$, $R^6$ and $R^7$ having the aforementioned definitions.

Preferably, in this embodiment n is 0.

Preferably, in this embodiment m is 0.

Preferably, in this embodiment $R^3$, $R^4$, $R^5$ and $R^6$ each represent a hydrogen atom.

Preferably, in this embodiment $R^2$ is:

a phenyl group unsubstituted or substituted by one or more substituents, the same or different, selected in particular from among:

$C_1$ to $C_6$ alkoxy group, preferably $C_1$ to $C_3$, straight-chain or branched e.g. methoxy, ethoxy, propoxy, iso-propoxy, butoxy, ter-butoxy;

a halogen atom e.g. fluorine, chlorine, bromine;

a pyridine group.

Preferably in this embodiment n is 0, m is 0, $R^3$, $R^4$, $R^5$ and $R^6$ each represent a hydrogen atom and $R^2$ is:

a phenyl group, unsubstituted or substituted by one or more substituents, the same or different, selected in particular from among:

$C_1$ to $C_6$ alkoxy group, preferably $C_1$ to $C_3$, straight-chain or branched e.g. methoxy, ethoxy, propoxy, iso-propoxy, butoxy, ter-butoxy;

a halogen atom e.g. fluorine, chlorine, bromine;

a pyridine group.

In one particular embodiment, in the compounds of formula (I), $R^1$ represents a group: —C(O)CR$^3$R$^4$CR$^5$R$^6$C(O)OH, m, n, $L^1$, $R^2$, $L^2$, $R^3$, $R^4$, $R^5$, $R^6$ and $R^7$ having the aforementioned definitions.

Preferably in this embodiment n is 0.

Preferably, in this embodiment m is 0.

Preferably, in this embodiment $R^3$, $R^4$, $R^5$ and $R^6$ each represent a hydrogen atom.

Preferably, in this embodiment $R^2$ is:
- a phenyl group, unsubstituted or substituted by one or more substituents, the same or different, selected in particular from among:
  - $C_1$ to $C_6$ alkoxy group, preferably $C_1$ to $C_3$, straight-chain or branched e.g. methoxy, ethoxy, propoxy, iso-propoxy, butoxy, ter-butoxy; or
  - a halogen atom e.g. fluorine, chlorine, bromine.

Preferably, in this embodiment n is 0, m is 0, $R^3$, $R^4$, $R^5$ and $R^6$ each representing a hydrogen atom and $R^2$ is:
- a phenyl group unsubstituted or substituted by one or more substituents, the same or different, selected in particular from among:
  - $C_1$ to $C_6$ alkoxy group, preferably $C_1$ to $C_3$, straight-chain or branched e.g. methoxy, ethoxy, propoxy, iso-propoxy, butoxy, ter-butoxy.

In one particular embodiment, in the formula (I) compounds, $R^1$ represents a group: —(CH$_2$)$_4$C(O)OH, m, n, $L^1$, $R^2$, $L^2$ and $R^7$ having the aforementioned definitions.

Preferably, in this embodiment n is 0.

Preferably, in this embodiment m is 0.

Preferably, in this embodiment $R^2$ is:
- a phenyl group, unsubstituted or substituted by one or more substituents, the same or different, selected in particular from among:
  - $C_1$ to $C_6$ alkoxy group, preferably $C_1$ to $C_3$, straight-chain or branched e.g. methoxy, ethoxy, propoxy, iso-propoxy, butoxy, ter-butoxy;
  - a halogen atom e.g. fluorine, chlorine, bromine;
- a pyridine group.

Preferably, in this embodiment n is 0, m is 0 and $R^2$ is:
- a phenyl group, unsubstituted or substituted by one or more substituents, the same or different, selected in particular from among:
  - $C_1$ to $C_6$ alkoxy group, preferably $C_1$ to $C_3$, straight-chain or branched e.g. methoxy, ethoxy, propoxy, iso-propoxy, butoxy, ter-butoxy;
  - a halogen atom e.g. fluorine, chlorine, bromine;
- a pyridine group.

All the general and preferred characteristics of the groups R1, R2, R3, R4, R5, R6, R7, L1, L2, n and m can be combined together.

Preferably, the formula (I) compound is selected from among:

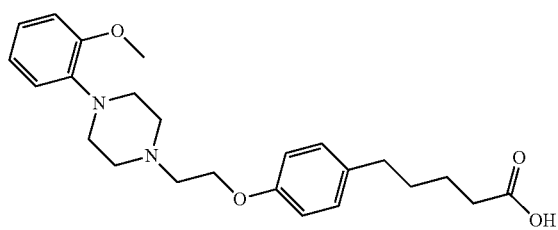 [SMILES: COc1ccccc1N1CCN(CCOc2ccc(CCCCC(=O)O)cc2)CC1]

-continued

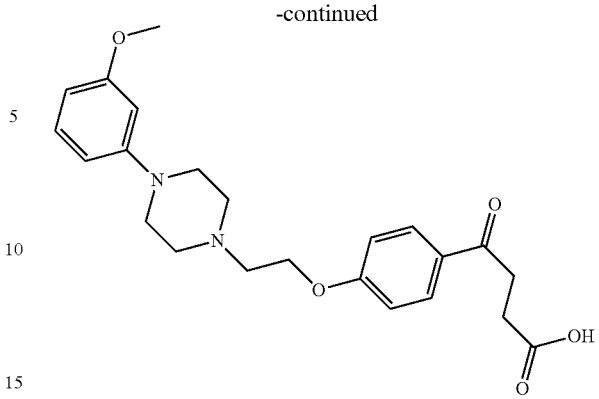

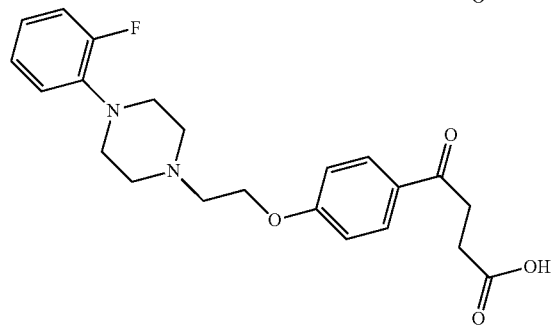

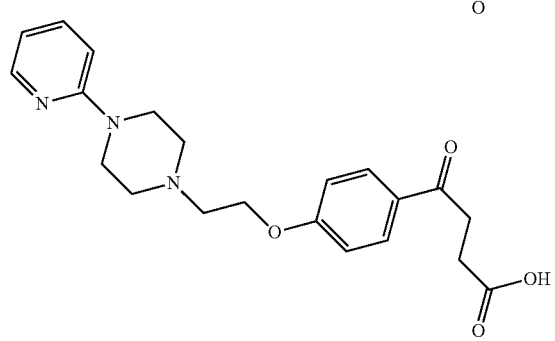

The invention also relates to compositions comprising solvates of the compounds of formulas (I).

The compounds of formulas (I) have a carboxylic function and can be salified. They can then be in the form of addition salts with organic or mineral bases. The addition salts with bases are pharmaceutically acceptable salts for example such as sodium salts, potassium salts, calcium salts, which are obtained using the corresponding hydroxides of alkaline and alkaline-earth metals as bases. As other type of addition salts with pharmaceutically acceptable bases mention can be made of salts with amines and in particular glucamine, N-methylglucamine, N,N-dimethylglucamine, ethanolamine, morpholine, N-methylmorpholine or lysine.

The compounds of formulas (I) can also be salified with mineral or organic acids and preferably with pharmaceutically acceptable acids such as hydrochloric, phosphoric, fumaric, citric, oxalic, sulfuric, ascorbic, tartaric, maleic, mandelic, methanesulfonic, lactobionic, gluconic, glucaric, succinic, sulfonic or hydroxypropanesulfonic acids.

Metformin may optionally be in the form of one of the pharmaceutically acceptable salts thereof. Particular can be made of the following forms: hydrochloride, acetate, benzoate, citrate, fumarate, embonate, chlorophenoxyacetate, glycolate, palmoate, aspartate, methanesulfonate, maleate, parachlorophenoxyisobutyrate, formate, lactate, succinate, sulfate, tartrate, cyclohexanecarboxylate hexanoate, octanoate, decanoate, hexadecanoate, octodecanoate, benzenesulfonate, trimethoxybenzoate, paratoluenesulfonate, adamantanecarboxylate glycoxylate, glutamate, pyrrolidonecarboxylate, naphthalene sulfonate, glucose-1-phosphate, nitrate, sulfite, dithionate, phosphate, preferably hydrochloride, fumarate, embonate, chlorophenoxyacetate.

The salts of metformin are obtained in manner known per se by persons skilled in the art, in particular by reaction between metformin and the acids corresponding to the above-mentioned salts.

These compositions may also comprise a pharmaceutically acceptable carrier and/or excipient.

The pharmaceutical compositions may be in any form known to those skilled in the art, in particular in forms intended for administration via parenteral, oral, rectal, permucosal or percutaneous route, preferably via oral route.

The compositions of the invention will be presented in the form of solutes or injectable suspensions or multi-dose bottles, in the form of coated or non-coated tablets, sugar-coated tablets, hard capsules, soft capsules, pills, tablets, powders, suppositories or rectal capsules, solutions or suspensions, for percutaneous use in a polar solvent or for permucosal use.

The excipients suitable for such routes of administration are derivatives of cellulose of microcrystalline cellulose, alkaline-earth carbonates, magnesium phosphate, starches, modified starches, lactose for solid forms.

For rectal use, cocoa butter or stearates of polyethylene glycol are the preferred excipients.

For parenteral use, water, aqueous solutes, physiological saline solution, isotonic solutes are the carriers having most practical use.

The invention also concerns the use of a composition of the invention to prepare a medicinal product.

The invention also concerns the composition of the invention for use thereof as medicinal product.

The invention also concerns the compositions of the invention intended for use in the treatment of pathologies associated with insulin-resistance syndrome (syndrome X). These pathologies are evidenced in particular in the publication by Haffner et al. (Diabetes, 1992, 41(6), 715-722).

The associations of metformin with other anti-diabetic compounds lead to saturation of response, and the actions of metformin and of anti-diabetic compounds do not always add to one another or not always in significant manner.

Most surprisingly, and advantageously, the association of metformin with the formula (I) compounds leads to accumulation of the separate actions of metformin and of the formula (I) compounds.

The present invention particularly concerns the pharmaceutical compositions of the invention for use thereof in the treatment of pathologies associated with insulin-resistance syndrome (syndrome X).

The present invention particularly concerns a method for treating pathologies associated with insulin-resistance syndrome, comprising the administration of an efficient amount of a pharmaceutical composition of the invention to a patient in need thereof.

The present invention particularly concerns the pharmaceutical compositions of the invention to prepare medicinal products for the treatment of pathologies associated with insulin-resistance syndrome.

Preferably, amongst the pathologies associated with insulin-resistance syndrome mention can be made of diabetes and in particular Type 2 diabetes.

Preferably, the compositions of the invention also allow inhibition of neoglucogenesis.

The present invention also concerns a composition of the invention or kit comprising at least one formula (I) compound or one of the salts thereof and metformin or a metformin salt for simultaneous, separate or sequential administration to a patient in need thereof. For simultaneous administration, the formula (I) compound and metformin may be in a mixture in the same preparation containing the same with a pharmaceutically acceptable carrier or excipient. They may also be packaged in separate preparations each with a pharmaceutically acceptable excipient or carrier, able to be mixed together in particular extemporaneously. For separate or sequential administration each of the active ingredients is packaged in its own preparation containing a pharmaceutically acceptable carrier or excipient.

Preferably, the composition or kit of the invention comprises metformin or one of the pharmaceutically acceptable salts thereof and a compound selected from among:

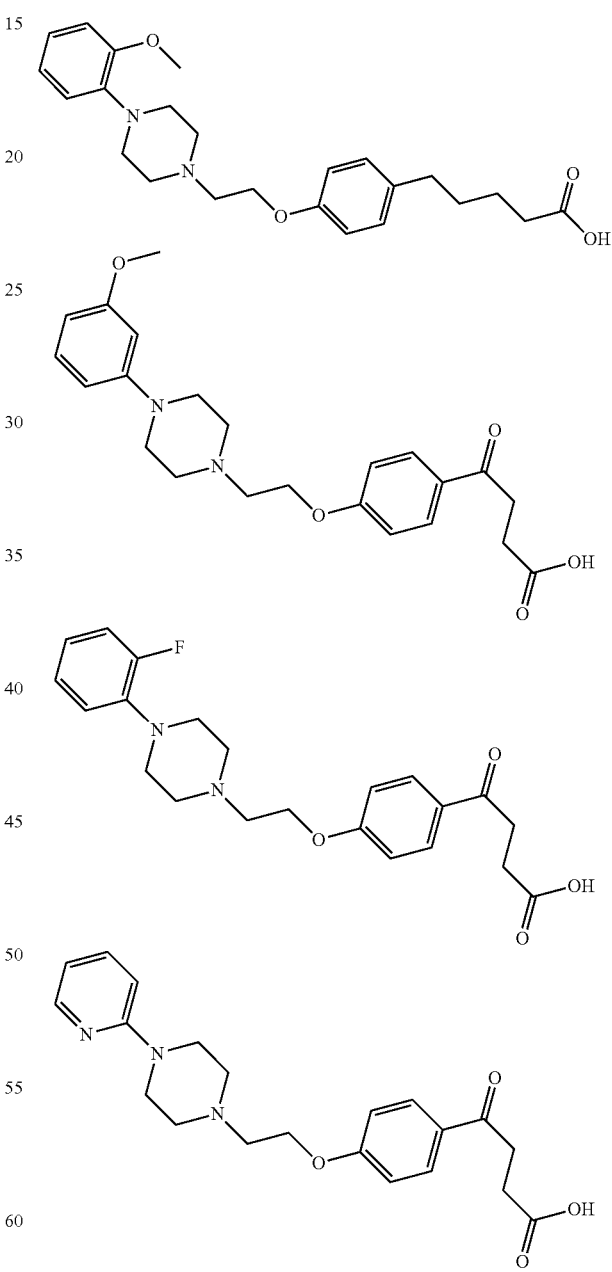

or one of the pharmaceutically acceptable salts thereof.

In one embodiment, the composition or kit of the invention comprises metformin or one of the pharmaceutically acceptable salts thereof and a compound of formula:

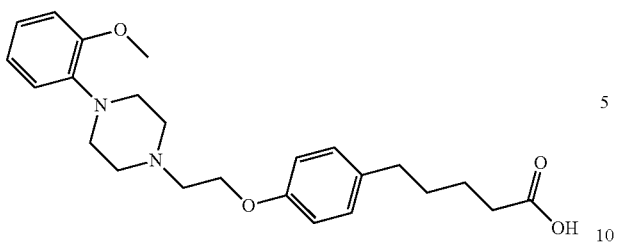

or one of the pharmaceutically acceptable salts thereof.

Preferably, the composition or kit of the invention comprises metformin or one of the pharmaceutically acceptable salts thereof and a compound selected from among:

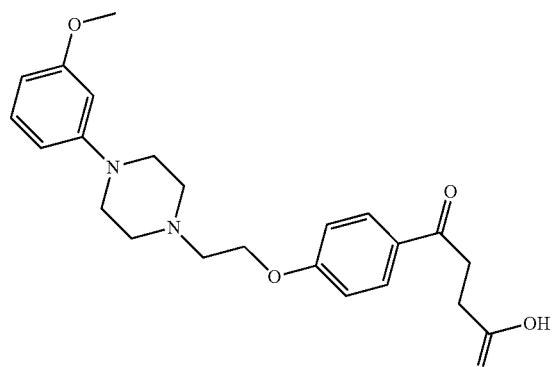

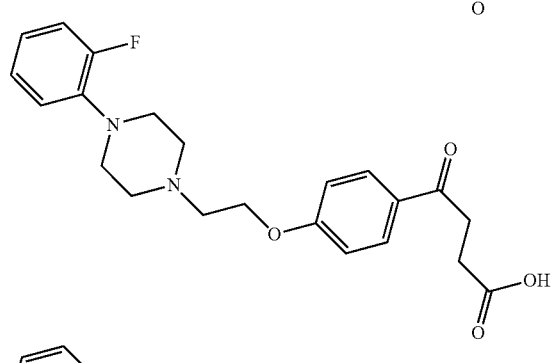

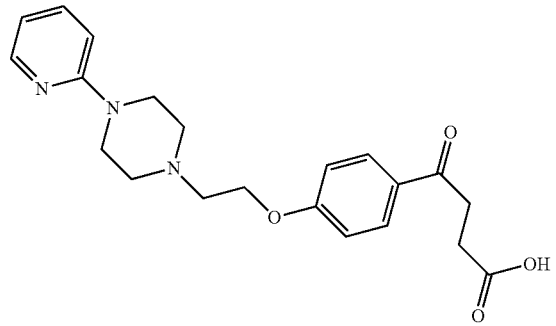

or one of the pharmaceutically acceptable salts thereof.

The dosage may vary within broad limits as a function of the therapeutic indication and route of administration, and in relation to the age and weight of the subject.

The identification of the patient in need of the above-indicated treatment is defined by persons skilled in the art. By patient is meant a human being or an animal. A physician or veterinary surgeon is able to identify via clinical tests, physical examination, biological assays or diagnosis and via family and/or medical history those individuals in need of such treatment.

By sufficient quantity is meant an amount of compound of the present invention that is efficient to prevent or treat pathological conditions. The sufficient quantity can be determined by those skilled in the art using conventional techniques and observation of results obtained under similar circumstances. To determine the sufficient quantity, different factors must be taken into consideration by skilled persons, in particular but not limited thereto: the subject, age, general state of health, disease concerned and degree of seriousness; the response of the subject, type of compound, route of administration, bioavailability of the administered composition, dosage, concomitant use with other medication, etc. Preferably, in the compositions of the invention the metformin/formula (1) compound ratio is such that the metformin is administered in an amount of 200 mg/day to 3 g/day and the compound of the invention is administered in an amount of 2.5 mg/day to 500 mg/day, preferably once or twice daily.

By polycarbocycle and polyheterocarbocycle according to the invention is meant polycyclic carbocycles and heterocarbocycles, in particular comprising two fused rings.

Preferably, and unless indicated otherwise, in the formula (I) compounds of the invention the polycarbocycles are 9- or 10-membered and are substituted or unsubstituted, preferably 10-membered, are aromatic and substituted or unsubstituted.

Preferably, and unless indicated otherwise, in the formula (I) compounds of the invention the polyheterocarbocycles have 9 or 10 members and may comprise 1, 2 or 3 heteroatoms, the same or different, selected in particular from among nitrogen, oxygen or sulfur, they are substituted or unsubstituted, saturated, partly unsaturated or aromatic, preferably aromatic. In particular, the polyheterocarbocycles represent

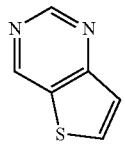

Preferably, and unless indicated otherwise, in the formula (I) compounds of the invention the carbocycles have 5 or 6 members, are saturated, partly unsaturated or aromatic, substituted or unsubstituted, preferably they have 6 members and are aromatic e.g. phenyl.

Preferably, and unless indicated otherwise, in the formula (I) compounds of the invention the heterocarbocycles have 5 or 6 members and may comprise 1, 2 or 3 heteroatoms, the same or different, selected in particular from among nitrogen, oxygen or sulfur, they are substituted or unsubstituted, saturated, partly unsaturated or aromatic, preferably aromatic. For example they are selected from among

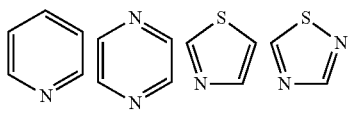

The formula (I) compounds (I) can be obtained using a process (P1) comprising:
(a) protection of the acid function (carried by $R^1$) of a compound of formula (II):

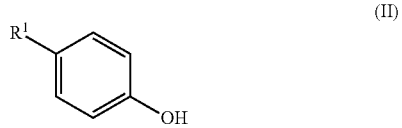

where $R^1$ is —C(O)CR³R⁴CR⁵R⁶C(O)OH or (CH₂)₄C(O)OH;

(b) reaction of the compound obtained at step (a) with a compound of formula $R^9$—(CH₂)₂—$R^8$ where $R^8$ and $R^9$, the same or different, represent a leaving group, preferably $R^9$ is more nucleofugal than $R^8$;

(c) reaction of the compound obtained at step (c) with a compound of formula (III)

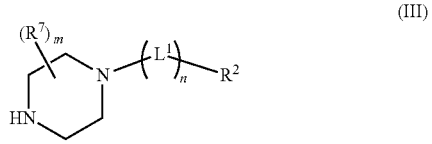

where $L^1$, n, m, $R^2$ and $R^7$ have the definitions given for formula (I);

(d) deprotection of the compound obtained at step (c).

The starting products are commercially available or can be easily prepared by persons skilled in the art on the basis of their general knowledge of organic chemistry.

The compounds for which $R^1$ represents C(OH)(H)CR³R⁴CR⁵R⁶C(O)OH can be obtained by reducing compounds for which $R^1$ represents C(O)CR³R⁴CR⁵R⁶C(O)OH. This reduction can be implemented for example in the presence of NaBH₄ in ethanol. This reduction can be performed for example between steps (b) and (c).

The compounds for which $R^1$ represents

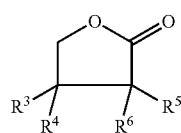

can be obtained by:
lactonization of the compounds for which $R^1$ represents —C(OH)(H)CR³R⁴CR⁵R⁶C(O)OH. This lactonization is conducted for example before step (c); or
lactonization of the compounds for which $R^1$ represents —C(O)CR³R⁴CR⁵R⁶C(O)OH. This lactonization is conducted for example after step (d).

These lactonizations can be performed using any method known to skilled persons, for example they can be performed in the presence of CF₃CO₂H in dichloromethane.

Step (a), corresponding to protection of the acid function, can be conducted in any manner known to skilled persons provided that protection is selective for the acid function in relation to the alcohol function. Among the protective groups of the carboxylic function, those generally described in Protective Groups in Organic Synthesis, Greene T. W. and Wuts P. G. M, published by John Wiley and Sons, 1991 and in Protective Groups, Kocienski P. J., 1994, Georg Thieme Verlag, are suitable. For example, it can be envisaged to protect the carboxylic function in ester form ($C_1$-$C_6$ alkyl, e.g. methyl). For example, step (a) can be performed by reaction of the formula (I) compound with methanol in the presence of an acid, sulfuric acid in particular.

Step (b) is preferably performed in an aprotic polar solvent such as acetonitrile, dimethylformamide (DMF), acetone, dimethylsulfoxide and halogenated hydrocarbons such as dichloromethane or dichloroethane, at a suitable temperature, in particular between 15 and 80° C., preferably between 15 and 35° C. One preferred solvent in particular is acetonitrile. Advantageously, this step takes place in the presence of a base such as potassium carbonate. Persons skilled in the art know that a leaving group is all the more labile the more the corresponding anionic species is stable. Therefore if $R^9$ is more nucleofugal than $R^8$ this corresponds to the fact that $R^{9-}$ is more stable than $R^{8-}$. The leaving groups $R^8$ and $R^9$, the same or different, are selected from among halogen atoms, preferably chlorine and bromine; ($C_6$-$C_{10}$) arylsulfonyloxy groups, the aryl group optionally being substituted by one or more $C_1$ to $C_6$ alkyl groups; ($C_1$-$C_6$) alkylsulfonyloxy groups wherein the alkyl group is optionally substituted by one or more halogen atoms. Preferably $R^8$ is chlorine and $R^9$ is bromine.

Step (c) is a nucleophilic substitution step for which the operating conditions can easily be determined by those skilled in the art. Advantageously the reaction is implemented in an aprotic polar solvent in the presence of a base. Examples of suitable solvents are acetonitrile, dimethylformamide, acetone, dimethylsulfoxide and halogenated hydrocarbons such as dichloromethane or dichloroethane. As base, mention can be made of carbonates of alkaline or alkaline-earth metals e.g. potassium carbonate. Advantageously the reaction at step (c) is conducted at a temperature of 50 to 120° C., for example under reflux of the solvent in the presence of an iodide of an alkaline metal such as potassium iodide. The amount of alkaline iodide may be variable and essentially depends on the type of reagents, type of solvent and reaction temperature. The reaction is generally stoichiometric, it is nonetheless possible to operate with a slight excess of one or other of the reagents.

The deprotection step (d) may be any deprotection known to persons skilled in the art and compatible with the protection implemented at step (a) allowing recovery of the acid function. For example, it may involve saponification in a basic, acid or catalytic (Pd/C) medium.

The formula (I) compounds can also be obtained using a second process (P2) comprising:
(i) reaction of a formula (III) compound with a compound of formula $R^9$—(CH₂)₂—$R^8$ where $R^8$ and $R^9$ are such as defined in process (P1);
(ii) protection of the acid function of a formula (II) compound;
(iii) reaction between the compound obtained at step (i) and the compound obtained at step (ii);
(iv) deprotection of the compound obtained at step (iii).

The starting products are commercially available or can easily be prepared by persons skilled in the art on the basis of their general knowledge of organic chemistry.

The compounds for which $R^1$ represents C(OH)(H)CR³R⁴CR⁵R⁶C(O)OH can be obtained by reducing compounds for which $R^1$ represents —C(O)CR³R⁴CR⁵R⁶C(O)OH. This reduction can be performed for example in the presence of NaBH₄ in ethanol. This reduction can be conducted for example between steps (ii) and (iii).

The compounds for which $R^1$ represents

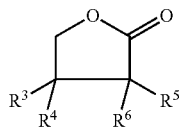

can be obtained by:
lactonization of the compounds for which $R^1$ represents —C(OH)(H)CR$^3$R$^4$CR$^5$R$^6$C(O)OH. This lactonization can take place for example before step (iii); or
lactonization of the compounds for which $R^1$ represents —C(O)CR$^3$R$^4$CR$^5$R$^6$C(O)OH. This lactonization can be performed for example after step (iv).

These lactonizations can be performed using any method known to persons skilled in the art, for example they can be performed in the presence of $CF_3CO_2H$ in dichloromethane.

An equilibrium generally exists between the forms for which $R^1$ represents —C(OH)(H)CR$^3$R$^4$CR$^5$R$^6$C(O)OH and the forms for which $R^1$ represents

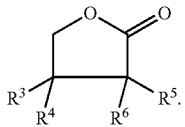

Step (i) is preferably implemented in an aprotic polar solvent such as acetonitrile, dimethylformamide (DMF), acetone, dimethylsulfoxide and halogenated hydrocarbons such as dichloromethane or dichloroethane, at an adapted temperature in particular between 15 and 80° C., preferably between 15 and 35° C. One preferred solvent in particular is acetonitrile. Advantageously, this step is conducted in the presence of a base such as potassium carbonate.

Step (ii), corresponding to protection of the acid function, can be conducted in any manner known to persons skilled in the art, provided that protection is selective for the acid function in relation to the alcohol function. Amongst the protective groups of the carboxylic function those generally described in Protective Groups in Organic Synthesis, Greene T. W. and Wuts P. G. M, published by John Wiley and Sons, 1991 and in Protective Groups, Kocienski P. J., 1994, Georg Thieme Verlag, are suitable. For example, the protection of the carboxylic function can be envisaged in ester form ($C_1$-$C_6$ alkyl e.g. methyl). For example step (a) can be conducted by reaction of the formula (I) compound with methanol in the presence of an acid, sulfuric acid in particular.

Step (iii) is a nucleophilic substitution step for which the operating conditions can easily be determined by those skilled in the art. Advantageously, the reaction is conducted in an aprotic polar solvent in the presence of a base. Examples of suitable solvents are acetonitrile, dimethylformamide, acetone, dimethylsulfoxide and halogenated hydrocarbons such as dichloromethane or dichloroethane. As base, mention can be made of carbonates of alkaline or alkaline-earth metals such as potassium carbonate. Advantageously the reaction at step (c) is conducted at a temperature of 50 to 120° C., for example under reflux of the solvent in the presence of an iodide of an alkaline metal such as potassium iodide. The amount of alkaline iodide may be variable and is essentially dependent on the type of reagents, the type of solvent and reaction temperature. The reaction is generally stoichiometric, but it is nevertheless possible to operate with a slight excess of one or other of the reagents.

The deprotection step iv) can be any deprotection known to persons skilled in the art and compatible with the protection performed at step (ii) allowing recovery of the acid function. For example it may be saponification in a basic, acid or catalytic (Pd/C) medium.

Advantageously, the formula (I) compounds of the invention act concomitantly on 3 target organs:
the liver via inhibition of hepatic gluconeogenesis (or neoglucogenesis);
skeletal muscle via stimulation of the glucose consumption thereof; and
the pancreas via stimulation of insulin secretion by beta cells.

Therefore the formula (I) compounds have the potential to correct the 3 major deficiencies observed in patients suffering from Type 2 diabetes.

The mechanism of action of the formula (I) compounds differs from that of metformin which allows a greater effect to be obtained from the association of the formula (I) compound+metformin than the effect obtained from metformin alone.

On the basis of these data and of the methods described below, persons skilled in the art, without any difficulty, will be able to confirm the additive effect of any formula (1) compound or more broadly to select any molecule able to be associated with metformin.

The present invention also concerns a method to select a compound for treating pathologies associated with insulin-resistance syndrome which provides an additional effect to the effect of metformin, comprising the steps of:
a) providing fasting, normal animals;
b) measuring glycaemia in these animals;
c) administering the compound to be tested to one portion of the animals, metformin to a second portion of the animals and an association of metformin and the compound to be tested to a last portion of the animals;
d) administering a glucose load to the animals, in particular of 2 to 4 g/kg animal body weight;
e) measuring glycaemia at different times;
f) determining whether the compound has an additive effect in addition to the effect of metformin on lowering of glycaemia, in particular comparing the glycaemia area under curve obtained for each of the compounds administered and determining whether the tested compound in association with metformin allowed a reduction in the glycaemia area under curve compared with metformin administered alone.

The method comprises a step g) to select the compound if it gives a positive response at step f).

The method may also comprise steps b), d) and e) conducted in batches of control animals that are not given any compound.

Preferably, the animals are normal, fasting mice, preferably Swiss mice e.g. 8-week old Swiss mice that have been fasting for 17 h in particular.

Preferably the administration of the compounds is given via oral route.

Preferably the glucose load is given via oral route.

Typically glycaemia is measured using a glucometer and glycaemia test strips.

Preferably the amount used of compound to be tested is between 1 and 200 mg/kg animal body weight.

Preferably, the amount of metformin used is between 300 mg/kg and 1000 mg/kg animal body weight.

Preferably, the association of metformin+compound to be tested comprises 300 to 1000 mg/kg animal body weight of metformin and 1 to 200 mg/kg animal body weight of compound to be tested.

According to one test condition the compound to be tested is or is not a formula (I) compound.

The selection method of the present invention may also comprise the prior steps of:
1) determining the toxicity of the compound to be tested;
2) providing liver cells of fasting animals;
3) incubating these cells with lactate or glutamine;
4) adding the compound to be tested to the incubation medium;
5) performing enzymatic assay of lactate or glutamine consumption and/or of glucose production and/or assay of ATP cell concentration;
6) determining which compounds are not or scarcely toxic allowing stimulation of complete oxidation of the lactate or glutamine and/or reduction of ATP cell concentration; and/or
7) providing animals having Type 2 diabetes;
8) administering the compound to be tested to these animals;
9) administering a glucose load in particular of 1 to 3 g/kg animal body weight;
10) evaluating the peripheral consumption of glucose by skeletal muscle and/or the concentration of circulating insulin;
11) determining which toxic or scarcely toxic compounds allow an increase in glucose consumption in the muscle and/or an increase in the concentration of circulating insulin.

The method may also comprise steps 3) and 5) and/or steps 9) and 10) conducted in batches of control animals not given any compound.

Preferably, administration of the compounds is via oral route.

Preferably, the glucose load is given via oral route.

Preferably, the cells at step 1) are liver cells of fasting rats, preferably fasting for 48 h.

Preferably, incubation is performed in the presence of 0.5 to 5 mM of lactate or glutamine.

Preferably, the compound to be tested is added in an amount of 0.5 to 2 mM.

The enzymatic assays of lactate or glutamine consumption, of glucose production and assay of ATP cell concentration are performed using methods well known to persons skilled in the art and in particular those described by Bergmeyer 1974.

Preferably the lactate used is $2\text{-}^{13}C$-lactate which allows better monitoring of its complete oxidation, in particular using carbon-13 spectroscopy.

The method of the invention then comprises either the implementation of steps 1) to 6) followed by implementation of steps a) to f) on those compounds responding positively at step 6), or the implementation of steps 7) to 11) followed by implementation of steps a) to f) on those compounds responding positively at step 11), or even the implementation of steps 1) to 11) followed by implementation of steps a) to f) on those compounds responding positively at steps 6) and 11).

The present invention also concerns a method to select non-toxic or scarcely toxic compounds allowing stimulation of complete lactate or glutamine oxidation and/or a reduction in ATP cell concentration, comprising the following steps of:

1) determining the toxicity of the compound to be tested;
2) providing liver cells of fasting animals;
3) incubating these cells with lactate or glutamine;
4) adding the compound to be tested to the incubation medium;
5) performing enzymatic assay of lactate or glutamine consumption and/or of glucose production and/or assay of ATP cell concentration;
6) determining those compounds that are not or scarcely toxic allowing stimulation of complete lactate or glutamine oxidation and/or a reduction in ATP cell concentration.

The method may also comprise steps 3) and 5) conducted in batches of control animals not given any compound.

The method comprises a step 7) to select the compound if it responds positively at step 6).

The present invention also concerns a method to select non-toxic or scarcely toxic compounds allowing an increase in glucose consumption by muscle and/or an increase in the concentration of circulating insulin, comprising the steps of:
1) determining the toxicity of the compound to be tested;
2) providing animals having Type 2 diabetes;
3) administering the compound to be tested to these animals;
4) administering a glucose load to the animals in particular of 1 to 3 g/kg animal body weight;
5) evaluating the peripheral consumption of glucose by skeletal muscle and/or the concentration of circulating insulin;
6) determining the non-toxic or scarcely toxic compounds allowing an increase in glucose consumption by muscle and/or an increase in the concentration of circulating insulin.

The method may also comprise steps 4) and 5) conducted in batches of control animals not given any compound.

The method comprises a step 7) to select the compound if it responds positively at step 6).

The present invention also concerns a method to select non-toxic or scarcely toxic compounds which allow stimulation of complete lactate or glutamine oxidation, a reduction in ATP cell concentration, an increase in glucose consumption by muscle and an increase in the concentration of circulating insulin, comprising the following steps of:
1) determining the toxicity of the compound to be tested;
2) providing liver cells of fasting animals;
3) incubating these cells with lactate or glutamine;
4) adding the compound to be tested to the culture medium
5) performing enzymatic assay of lactate or glutamine consumption and assay of ATP cell concentration;
6) determining the compounds that are not or scarcely toxic allowing stimulation of complete lactate or glutamine oxidation without increasing the ATP cell concentration; and
7) providing animals having Type 2 diabetes;
8) administering the compound to be tested to these animals;
9) administering a glucose load to the animals, in particular of 1 to 3 g/kg animal body weight;
10) evaluating the peripheral consumption of glucose by skeletal muscle and the concentration of circulating insulin;
11) determining those non-toxic or scarcely toxic compounds allowing an increase in glucose consumption by muscle and an increase in the concentration of circulating insulin.

The method may also comprise steps 3), 5), 9) and 10) conducted in batches of control animals not given any compound.

The method comprises a step 12) to select the compound if it responds positively at step 11).

The present invention also concerns a method for producing a composition comprising in association metformin or a salt of metformin and at least one compound having an additive effect adding to the effect of metformin, for example a formula (I) compound, the enantiomers, diastereoisomers and pharmaceutically acceptable salts thereof, wherein there is associated with metformin a compound having responded positively to the selection method just described, in its different configurations, or else the compound is subjected to this selection method, and if the compound proves to have a positive response to the test it is retained for the composition. This production method may comprise the association of the compound and of metformin in one same composition or in two separate compositions to be administered to the same patient, for example associated in a kit.

The present invention is now described with the help of non-limiting examples.

EXAMPLE 1

General Scheme for Preparing Compounds in which R¹ Represents C(O)CR³R⁴CR⁵R⁶C(O)OH

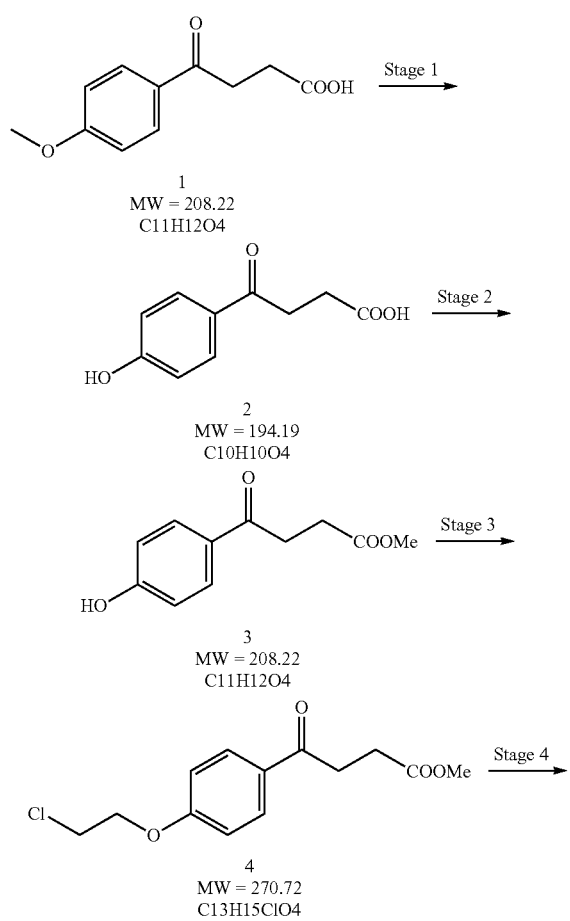

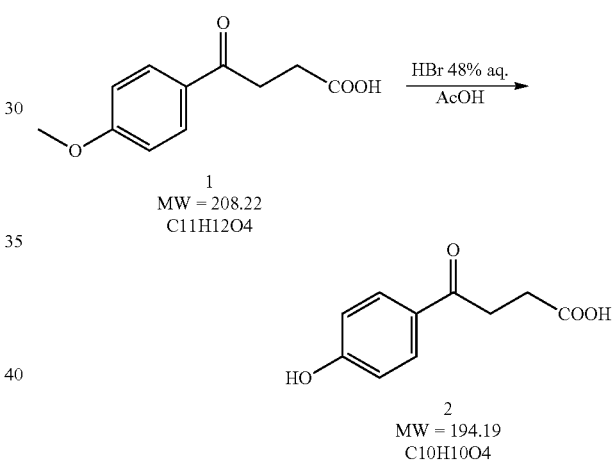

The first step is a demethylation step which can be performed by reacting HBr in an acetic acid medium.

The second step is an esterification reaction which can be performed by reaction with methanol in the presence of sulphuric acid.

Steps 3 and 4 are nucleophilic substitution steps.

Step 5 can be conducted in particular via acid hydrolysis or saponification.

Step 1: Demethylation

Equipment: 1 L Round-Bottomed Flask Equipped with Magnetic Agitation and Coolant—Oil Bath.

4-(4-methoxyphenyl)-4-oxobutanone 1 (40 g) is placed in solution in acetic acid (360 ml) and 48% aqueous hydrobromic acid (120 ml). The reaction medium is heated to 130° C. overnight.

The progress of the reaction is monitored by TLC (eluting with heptane/ethyl acetate 1:1). After overnight agitation under these conditions, the starting ether 1 is seen to disappear to the benefit of a more polar product.

The reaction medium is concentrated to dryness under reduced pressure. The residue obtained is re-dissolved in water and the aqueous phase extracted three times with ethyl acetate. Once combined, the organic phases are washed once with saturated sodium chloride solution, dried over magnesium sulfate, filtered and concentrated under reduced pressure to afford a solid (38 g).

$^{1H}$NMR analysis of the reaction mixture reveals the presence of the expected phenol 2 in a mixture with about 6% of starting ether.

Quantitative yield.

Step 2: Esterification

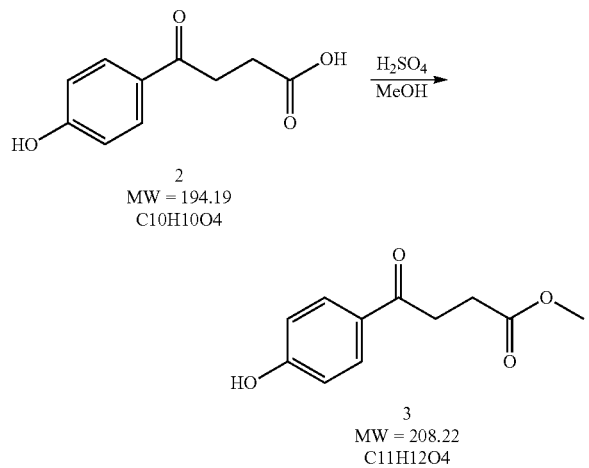

Equipment: 1 L Three-Necked Flask Equipped with Magnetic Agitation, Coolant and Placed Under a Stream of Nitrogen—Oil Bath.

The derivative 4-(4-hydroxyphenyl)-4-oxobutanoic acid 2 (48 g) is placed in solution in methanol (480 ml) before slow pouring of sulfuric acid (48 ml). The solution obtained is heated to 70° C. overnight.

The progress of the reaction is monitored by TLC (eluting with heptane/ethyl acetate 1:1). After overnight agitation under these conditions, the starting acid 2 is seen to disappear to the benefit of a less polar product.

The reaction medium is concentrated to dryness under reduced pressure. The residue obtained is re-dissolved in water (500 ml) and dichloromethane (500 ml). The heterogeneous medium is carefully neutralised with a saturated solution of sodium hydrogen carbonate (pH 7-8). The aqueous phase is then extracted three times with ethyl acetate. Once combined, the organic phases are washed with saturated sodium chloride solution, dried over magnesium sulfate, filtered and concentrated under reduced pressure to afford a solid (49.6 g).

$^{1H}$NMR analysis of the reaction mixture reveals the presence of the expected ester 3 in a mixture with less than 3% of the compound methyl 4-(4-methoxyphenyl)-4-oxobutanoate.

Yield: 96%.

Step 3: Nucleophilic Substitution

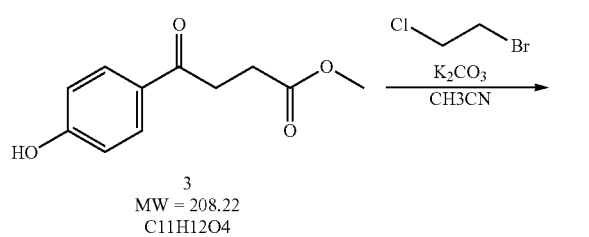

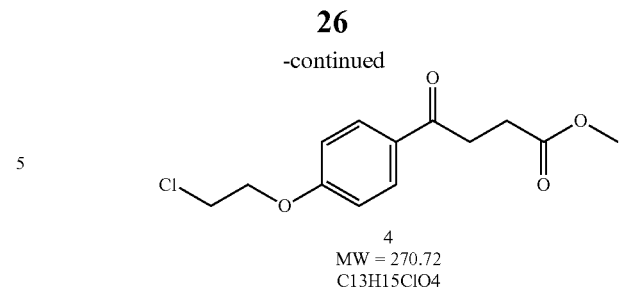

Equipment: 1 L Three-Necked Flask Equipped with Magnetic Agitation, Coolant and Placed Under a Stream of Nitrogen—Oil Bath.

The methyl 4-(4-hydroxyphenyl)-4-oxobutanoate 3 (49.6 g) is placed in solution in acetonitrile (400 ml). Potassium carbonate (98.77 g) is added to the solution. The reaction medium is heated to 50° C. before pouring a solution of 1-bromo-2-chloroethane (102.5 g) in acetonitrile (170 ml). The reaction medium is heated to 80° C. overnight.

The progress of the reaction is monitored by TLC (eluting with heptane/ethyl acetate 7:3). After an agitation time of 24 h under these conditions compound 3 is seen to disappear to the benefit of a less polar product.

After return to ambient temperature, the reaction medium is filtered to remove the potassium carbonate. The potassium carbonate is rinsed with acetonitrile and the filtrate is concentrated to dryness under reduced pressure. The residue obtained is re-dissolved in water (500 ml) and the aqueous phase is extracted twice with ethyl acetate (600 ml). The organic phases are combined, washed once with 1M sodium hydroxide solution (400 ml), dried over magnesium sulfate, filtered and concentrated under reduced pressure to afford a beige solid (61.44 g).

$^{1H}$NMR analysis of the reaction mixture reveals the presence of the expected chlorinated derivative 4.

Yield: 95%.

Step 4: Nucleophilic Substitution

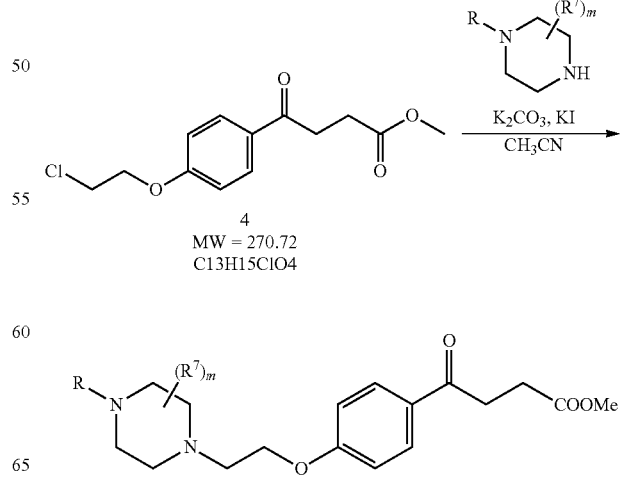

Equipment: Stem Apparatus Equipped with Heating System and Orbital Agitation, 9 ml Reactors—Manifold—Multivac Evaporation System—Allexis Extraction Apparatus Under a stream of nitrogen, the chlorinated derivative 4 (500 mg, 1.85 mmol, 1 eq.) is distributed over the different reactors and placed in solution in acetonitrile (5 ml) in the presence of R-piperazine (1.85 mmol, 1 eq.), previously dried potassium carbonate (766 mg, 5.54 mmol, 3 eq.), potassium iodide (307 mg, 1.85 mmol, 1 eq.). After passing a stream of nitrogen the reactors are closed and heated to 80° C.

After 72 hours heating is halted. On return to ambient temperature the different reaction media are filtered in parallel on Supelco cartridges connected to a Manifold to remove the inorganic salts. After rinsing with acetonitrile, the filtrates are concentrated to dryness under reduced pressure using the Multivac. The residues obtained are re-dissolved in water (20 ml) and extracted three times in parallel on the Allexis apparatus with ethyl acetate (10 ml). The different organic phases are combined, dried over magnesium sulfate, filtered and concentrated under reduced pressure using the Multivac.

The different reaction mixtures are purified on a prepacked Redisep 40 g chromatography column, Biotage SP4 system, using a dichloromethane/methanol gradient.

Step 5: Acid Hydrolysis

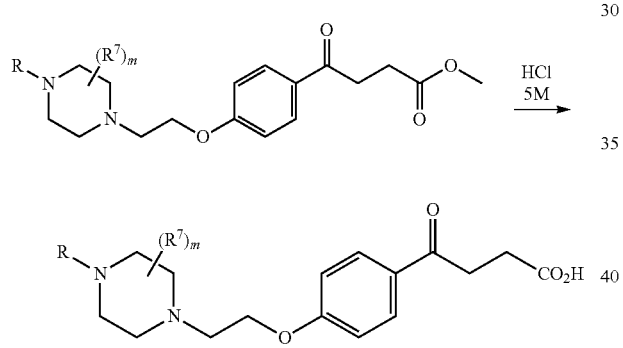

Equipment: Syncore—Heating System—Orbital Agitation—50 ml Reactors

The different esters are placed in solution in hydrochloric acid 5 and the solutions heated to 90° C. for 2 hours. TLC monitoring (eluting with dichloromethane/methanol 98:2, UV detection) of the reaction medium in each reactor allows verification that the esters have disappeared to the benefit of more polar products.

The reaction media are concentrated to dryness under reduced pressure in the Multivac. The solids obtained are triturated with acetone (10V) then filtered through a sintered filter and dried in vacuo.

Step 5: Saponification

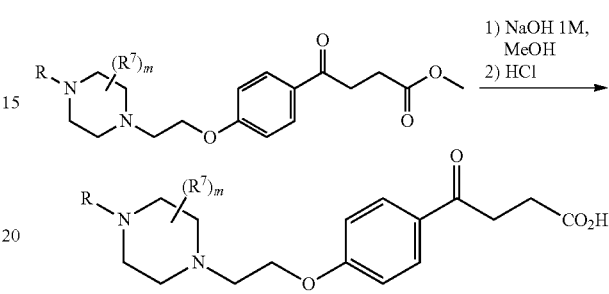

Equipment: Radley Equipped with Reactors and Magnetic Agitation.

The different esters are placed in solution in methanol (4V) in the presence of 1M sodium hydroxide solution (8V). After overnight agitation under these conditions TLC monitoring (eluting with dichloromethane/methanol 98:2, UV detection) allows verification of the disappearance of the esters to the benefit of more polar products.

After concentration of the methanol, the different aqueous solutions are extracted with ethyl acetate (5 ml) and acidified to pH 1 with 3M hydrochloric acid solution.

The acids are then isolated via desalination by eluting the different aqueous solutions on Porapak Rxn resin.

Desalination protocol:

Condition the resin with 45 ml methanol

Deposit the aqueous phase (4 to 5 ml)

Rinse with 100 ml methanol

Elute with 100 ml of 2M ammonia solution in methanol

Concentrate to dryness under reduced pressure.

The solids obtained after desalination are triturated with ethyl ether or recrystallized in acetonitrile.

The following compounds were obtained by implementing the general scheme of Example 1 (Step 5 acid hydrolysis).

| Yield: 95% | Structure: | Compound 1 |
|---|---|---|
| | 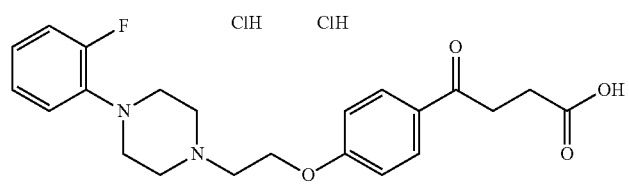 [SMILES: Cl ; Cl ; O=C(O)CCC(=O)c1ccc(OCCN2CCN(c3ccccc3F)CC2)cc1] | Molecular weight: 473.38<br>Molecular formula: $C_{22}H_{27}Cl_2FN_2O_4$<br>Form/colour: White solid |

$^{1H}$NMR (DMSO, 300 MHz, δ ppm): 2.56 (t, 2H); 3.18-3.41 (m, 6H); 3.50 (d, 2H); 3.63-3.70 (m, 4H); 4.59 (t, 2H); 7.00-7.23 (m, 6H); 7.99 (d, 2H); 11.49 (broad s, 1H)

MS (ESI): 401.10 (MH$^+$); 399.2 (MH$^-$) base form

Yield: 93%  Structure:  Compound 2

Molecular weight: 456.37
Molecular formula: $C_{21}H_{27}Cl_2N_3O_4$
Form/colour: White solid $^{1H}$NMR (DMSO, 300 MHz, δ ppm): 2.56 (t, 2H); 3.18-3.32 (m, 4H); 3.42-3.52 (m, 2H); 3.62-3.72 (m, 4H); 4.45 (d, 2H); 4.55 (t, 2H); 6.88 (t, 1H); 7.12-7.18 (m, 3H); 7.80-7.85 (m, 1H); 8.00 (d, 2H); 8.14 (d, 1H); 11.24 (broad s, 1H)
MS (ESI): 384.30 (MH$^+$); 382.20 (MH$^-$) base form Yield: 99%  Structure:  Compound 3

Molecular weight: 485.41
Molecular formula: $C_{23}H_{30}Cl_2N_2O_5$
Form/colour: White solid $^{1H}$NMR (DMSO, 300 MHz, δ ppm): 2.56 (t, 2H); 3.12-3.33 (m, 6H); 3.61-3.67 (m, 4H); 3.73 (s, 3H); 3.84 (d, 2H); 4.57 (t, 2H); 6.45 (dd, 1H); 6.53 (s, 1H); 6.58 (dd, 1H); 7.10-7.19 (m, 3H); 8.00 (d, 2H); 11.21 (broad s, 1H)
MS (ESI): 413.20 (MH$^+$); 411.20 (MH$^-$) base form

EXAMPLE 2

General Scheme for the Preparation of Compounds Wherein $R^1$ Represents —$(CH_2)_4C(O)OH$

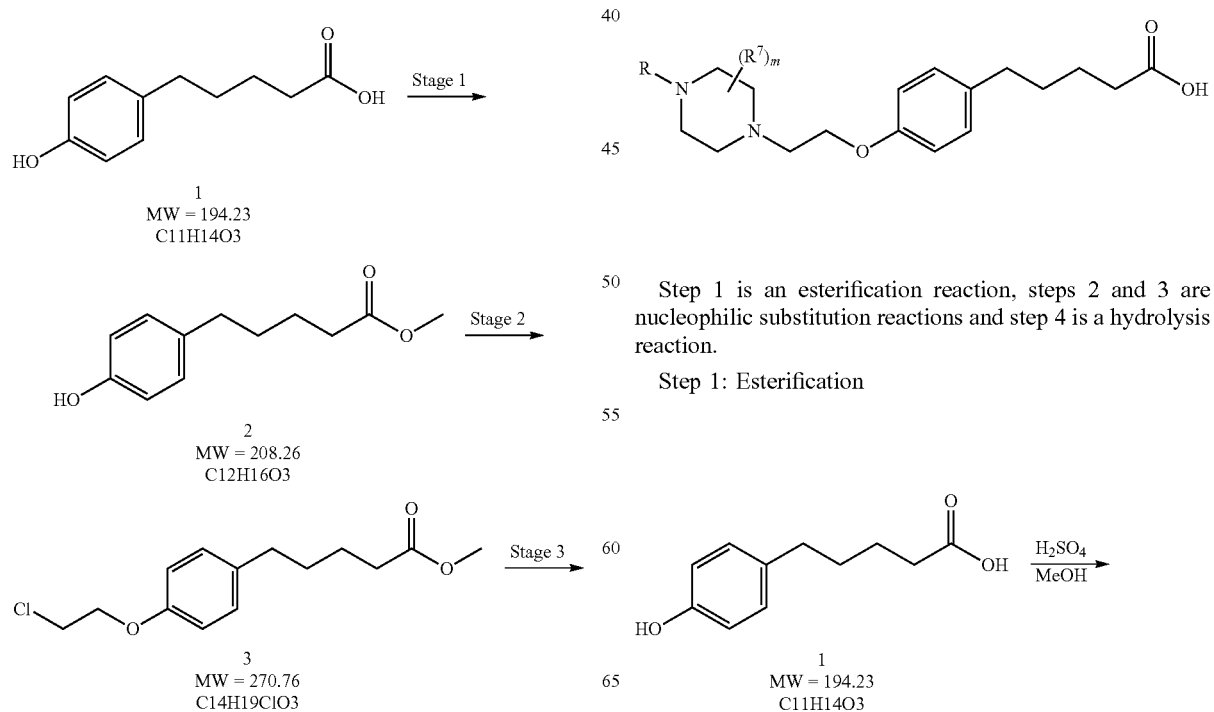

Step 1 is an esterification reaction, steps 2 and 3 are nucleophilic substitution reactions and step 4 is a hydrolysis reaction.

Step 1: Esterification

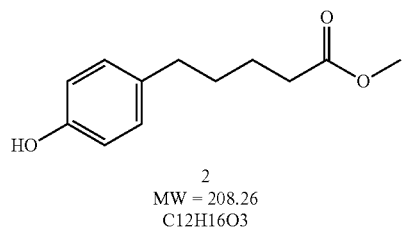

2
MW = 208.26
C12H16O3

Equipment: 500 ml Three-Necked Flask Equipped with Magnetic Agitation, Coolant and Placed Under a Stream of Nitrogen—Oil Bath.

5-(4-hydroxyphenyl)-pentanoic acid 1 (25 g) is placed in solution in methanol (37 5 ml) before slow pouring of sulfuric acid (25 ml). The solution obtained is heated to 65° C. overnight. The progress of the reaction is monitored by TLC (eluting with heptane/ethyl Acetate 1:1). After overnight agitation under these conditions the starting acid 1 is seen to disappear to the benefit of a less polar product.

The reaction medium is concentrated to dryness under reduced pressure. The residue obtained is re-dissolved in dichloromethane (300 ml). The heterogeneous medium is neutralised and basified with precaution with saturated sodium hydrogen carbonate solution (pH 8-9). The aqueous phase is then extracted three times with dichloromethane. Once combined, the organic phases are washed once with saturated sodium chloride solution, dried over magnesium sulfate, filtered and concentrated under reduced pressure to afford a pinkish oil (27 g).

Yield: 99%

Step 2: Nucleophilic Substitution

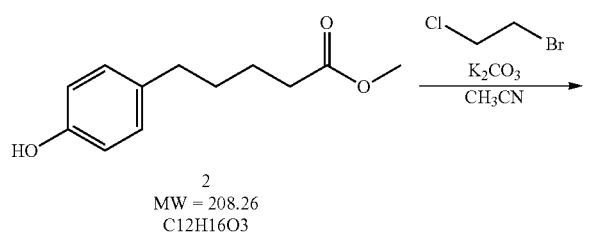

2
MW = 208.26
C12H16O3

3
MW = 270.76
C14H19ClO3

Equipment: 500 ml Three-Necked Flask Equipped with Magnetic Agitation, Coolant and Placed Under a Stream of Nitrogen—Oil Bath.

The ester methyl 5-(4-hydroxyphenyl)-pentanoate 2 (26.8 g) is placed in solution in acetonitrile (250 ml). Previously dried potassium carbonate (53.36 g) is added to the solution. The reaction medium is heated to 50° C. before slow pouring of a solution of 1-bromo-2-chloroethane (55.36 g) in acetonitrile (60 ml). The reaction medium is heated to 80° C. overnight.

The progress of the reaction is monitored by TLC (eluting with heptane/ethyl Acetate 7:3). After an agitation time of 24 h under these conditions the presence of phenol 2 is still observed. An additional quantity of 1-bromo-2-chloroethane (9.23 g, 64.3 mmol, 0.5 eq.) is added and the reaction medium is held under agitation at 80° C. for a further 24 h. TLC monitoring shows that the reaction does not change. NMR of the proton of an aliquot of the reaction medium allows quantification of the compounds 2 and 3 in a ratio of the order of 33:66.

On return to ambient temperature, the reaction medium is filtered to remove the potassium carbonate. The potassium carbonate is rinsed with ethyl acetate and the filtrate is concentrated to dryness under reduced pressure. The residue obtained is re-dissolved in water (100 ml) and the aqueous phase is extracted three times with ethyl acetate (100 ml). The organic phases are combined, washed with 1M sodium hydroxide solution (200 ml) then with water (100 ml), dried over magnesium sulfate, filtered and concentrated under reduced pressure to afford a beige oil (39.5 g).

$^{1H}$NMR analysis of the reaction mixture reveals the presence of the expected chlorinated derivative 3 in a mixture with close to 30% of raw material 2.

The reaction mixture is purified by chromatography on silica gel (1 L). The compounds to be separated are eluted using a heptane/ethyl acetate gradient.

The desired compound is isolated in oil form (22.4 g).

Yield: 64%

Step 3: Nucleophilic Substitution

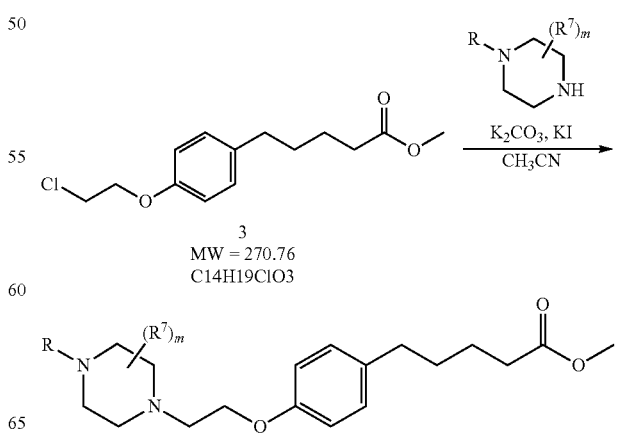

3
MW = 270.76
C14H19ClO3

Equipment: Stem Apparatus Equipped with Heating System and Orbital Agitation. 9 ml Reactors—Manifold—Multivac Evaporation System—Allexis Extraction Apparatus Under a stream of nitrogen, the chlorinated derivative 3 (500 mg, 1.85 mmol, 1 eq.) is distributed over the different reactors and placed in solution in acetonitrile (5 ml) in the presence of R-piperazine (1.85 mmol, 1 eq.), previously dried potassium carbonate (766 mg, 5.54 mmol, 3 eq.) and potassium iodide (307 mg, 1.85 mmol, 1 eq.). After passing a stream of nitrogen the reactors are closed and heated to 80° C.

After 72 hours the heating is halted. On return to ambient temperature the different reaction media are filtered in parallel on Supelco cartridges connected to a Manifold to remove the inorganic salts. After rinsing with acetonitrile the filtrates are concentrated to dryness under reduced pressure using the Multivac. The residues obtained are re-dissolved in water (20 ml) and extracted three times in parallel on Allexis apparatus with ethyl acetate (10 ml). The different organic phases are combined, dried over magnesium sulfate and concentrated under reduced pressure using the Multivac.

The different reaction mixtures are purified by chromatography on a pre-packed Redisep 40 g column, Biotage SP4 system, using a dichloromethane/methanol gradient.

Step 4: Hydrolysis

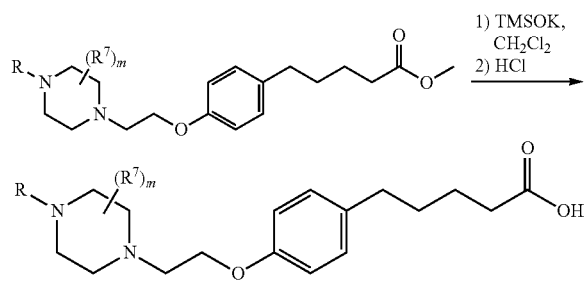

Equipment: Stem Apparatus Equipped with Heating System and Orbital Agitation. 9 ml Reactors—Multivac Evaporation System.

The different esters derived from 3 are placed in solution in dichloromethane (5 ml) in the presence of potassium trimethylsilanoate. The reaction medium is heated to 35° C. overnight. After overnight agitation under these conditions, TLC monitoring (eluting with dichloromethane/methanol 98:2, UV detection) allows verification that the esters have disappeared to the benefit of more polar products.

The different reaction media are concentrated to dryness under reduced pressure. The residues obtained are triturated with a mixture of diethyl ether (4 volumes) and ethanol (2 volumes) to remove excess potassium trimethylsilanoate and residual trimethylmethoxysilane. After filtration, the potassium carboxylates are isolated and dried under reduced pressure.

Each potassium carboxylate is placed in solution in a minimum amount of distilled water (1 to 11 ml) before adding 1N hydrochloric acid solution (2 eq.). After an agitation time of 30 minutes, the acids obtained precipitate in the form of a gum. Each acid is regularly triturated until the onset of a powdery precipitate. The precipitates are filtered, washed once with water then dried under reduced pressure in the presence of $P_2O_5$.

The following compounds were obtained by implementing the general scheme of Example 2

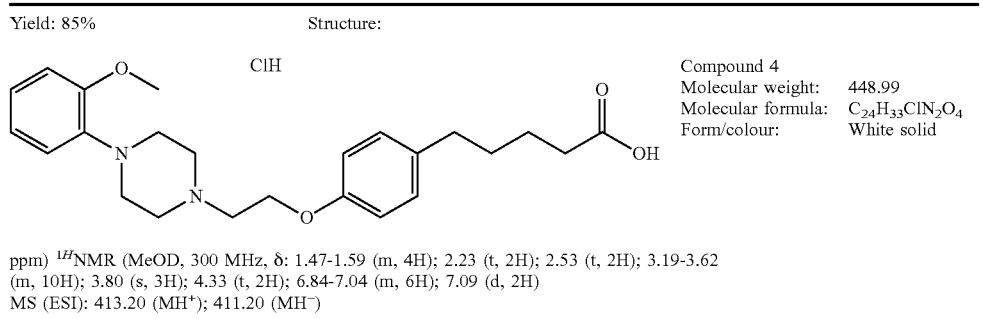

Yield: 85%    Structure:

Compound 4
Molecular weight: 448.99
Molecular formula: $C_{24}H_{33}ClN_2O_4$
Form/colour: White solid ppm) $^{1H}$NMR (MeOD, 300 MHz, δ: 1.47-1.59 (m, 4H); 2.23 (t, 2H); 2.53 (t, 2H); 3.19-3.62 (m, 10H); 3.80 (s, 3H); 4.33 (t, 2H); 6.84-7.04 (m, 6H); 7.09 (d, 2H)
MS (ESI): 413.20 (MH$^+$); 411.20 (MH$^-$)

EXAMPLE 3

Study on the Additive Anti-Diabetic Action in Swiss Mice Between Metformin and Various Compounds in the Metabolys Portfolio The anti-diabetic action of the compounds in Examples 1 and 2 were determined via oral route in normal Swiss mice fasting for 17 hours.

The mice used were aged 8 weeks. The animals were housed for a minimum time of one week after delivery (ordered from Charles River France) up until the day of experimentation in an animal facility at a temperature regulated at 21-22° C. and subjected to a light cycle (from 9 h to 17 h) and dark cycle (from 19 h to 7 h). They were fed a maintenance diet: water and food were provided « ad libitum ».

The animals were treated via oral route 1 hour before oral administration of a glucose load (oral glucose tolerance test—OGTT). Glycaemia was measured at various times before and after this glucose load. This glycaemia was measured using a glucometer (Lifescan OneTouch Ultra, Lifescan, Johnson and Johnson Company) and OneTouch Ultra glycaemia test strips.

In the Tables below n represents the number of mice included in the study.

1. Study on the additive effect of compound 1 (50 mg/kg per os) adding to the effect of metformin (300 mg/kg per os) on changes in glycaemia levels after an oral glucose load (OGTT) in Swiss mice fasting for 17 hours.

TABLE 1

Additive effect of compound 1 with metformin on glycaemia (mM/liter) in Swiss mice fasting for 17 h during a glucose tolerance test.

| Experimental conditions | Glycaemia Time (mn) | | | | | |
|---|---|---|---|---|---|---|
| | −60 | 0 | 30 | 60 | 90 | 120 |
| Carrier (n = 5) | 4.4 ± 0.3 | 4.8 ± 0.4 | 19.5 ± 1.2 | 15.1 ± 1.5 | 10.1 ± 0.9 | 7.8 ± 0.8 |
| Compound 1 (50 mg/kg) (n = 5) | 5.0 ± 0.2 | 4.5 ± 0.3 | 15.2 ± 1.9 | 10.6 ± 0.2 | 6.5 ± 0.5 | 5.3 ± 0.2 |
| Metformin (300 mg/kg) (n = 5) | 3.7 ± 0.3 | 3.2 ± 0.3 | 8.6 ± 0.5 | 9.4 ± 0.8 | 7.7 ± 1.0 | 6.2 ± 0.8 |
| Compound 1 (50 mg/kg) + Metformin (300 mg/kg) (n = 5) | 3.9 ± 0.2 | 3.0 ± 0.3 | 7.8 ± 1.0 | 4.5 ± 0.8 | 3.8 ± 0.6 | 2.6 ± 0.6 |

The 2 compounds were administered successively one hour before the glucose load. All the groups were composed of 5 mice (metformin alone, compound 1 alone, metformin+ compound 1, control group with the carrier alone). Blood samples were taken at 0, 30, 60, 90 and 120 minutes after the glucose load.

After administration of the glucose load, metformin alone caused the glycaemia area under curve to drop by 44.2%, compound 1 alone by 42.5% and the metformin plus compound combination by 79.5%.

These results show a major effect of the compositions of the invention on changes in glycaemia.

2. Study on the additive effect of compound 2 (50 mg/kg per os) adding to the effect of metformin (300 mg/kg per os) on changes in glycaemia levels after an oral glucose load (OGTT) in Swiss mice fasting for 17 hours.

TABLE 2

Additive effect of compound 2 with metformin on glycaemia (mM/liter) in Swiss mice fasting for 17 h during a glucose tolerance test.

| Experimental conditions | Glycaemia Time (mn) | | | | | |
|---|---|---|---|---|---|---|
| | −60 | 0 | 30 | 60 | 90 | 120 |
| Carrier (n = 4) | 4.4 ± 0.2 | 5.2 ± 0.4 | 19.6 ± 2.9 | 18.7 ± 2.9 | 9.3 ± 1.2 | 7.1 ± 0.6 |
| Compound 2 (50 mg/kg) (n = 4) | 4.6 ± 0.4 | 4.9 ± 0.2 | 14.5 ± 1.4 | 10.4 ± 0.5 | 8.3 ± 1.1 | 6.8 ± 0.6 |
| Metformin (300 mg/kg) (n = 4) | 3.8 ± 0.1 | 3.6 ± 0.3 | 11.2 ± 0.3 | 9.5 ± 0.4 | 8.0 ± 1.3 | 8.2 ± 0.7 |
| Compound 2 (50 mg/kg) + Metformin (300 mg/kg) (n = 4) | 4.5 ± 0.5 | 3.8 ± 0.3 | 7.3 ± 1.8 | 5.9 ± 1.8 | 4.9 ± 1.3 | 4.1 ± 0.7 |

The 2 compounds were administered successively one hour before the glucose load. All the groups were composed of 4 mice (metformin alone, compound 2 alone, metformin+ compound 2, control group with carrier alone). Blood samples were taken at 0, 30, 60, 90 and 120 minutes after the glucose load.

After the glucose load, metformin alone caused the glycaemia area under curve to drop by 38.7%, compound 2 by 40.5% and the combination of metformin plus compound 2 by 76.8%.

These results show a major effect of the compositions of the invention on changes in glycaemia.

3. Study on the additive effect of compound 3 (50 mg/kg per os) adding to the effect of metformin (300 mg/kg per os) on changes in glycaemia levels after an oral glucose load (OGTT) in Swiss mice fasting for 17 hours.

TABLE 3

Additive effect of compound 3 with metformin on glycaemia (mM/liter) in Swiss mice fasting for 17 h during a glucose tolerance test.

| Experimental condition | Glycaemia Time (mn) | | | | | |
|---|---|---|---|---|---|---|
| | −60 | 0 | 30 | 60 | 90 | 120 |
| Carrier (n = 4) | 4.7 ± 0.4 | 5.4 ± 0.3 | 17.2 ± 2.1 | 15.4 ± 2.1 | 10.5 ± 1.4 | 8.3 ± 0.7 |
| Compound 3 (50 mg/kg) (n = 4) | 4.4 ± 0.3 | 5.5 ± 0.3 | 11.3 ± 0.6 | 9.7 ± 0.4 | 7.4 ± 0.3 | 7.2 ± 0.5 |
| Metformin (300 mg/kg) (n = 4) | 5.6 ± 0.3 | 6.0 ± 0.3 | 9.2 ± 0.8 | 8.2 ± 0.4 | 7.7 ± 0.2 | 9.6 ± 0.8 |
| Compound 3 (50 mg/kg) + Metformin (300 mg/kg) (n = 4) | 5.4 ± 0.4 | 5.4 ± 0.3 | 8.4 ± 0.7 | 7.7 ± 0.7 | 7.0 ± 1.5 | 6.5 ± 1.2 |

The 2 compounds were successively administered one hour before the glucose load. All the groups were composed of 5 mice (metformin alone, compound 3 alone, metformin+compound 3, control group with carrier alone). Blood samples were taken at 0, 30, 60, 90 and 120 minutes after the glucose load.

After the glucose load, metformin alone caused the glycaemia area under curve to drop by 68.5%, compound 3 alone by 54.9% and the combination metformin plus compound 3 by 74.4%.

These results show a major effect of the compositions of the invention on changes in glycaemia levels.

4. Study on the additive effect of compound 4 (50 mg/kg per os) adding to the effect of metformin (300 mg/kg per os) on changes in glycaemia levels after an oral glucose load (OGTT) in Swiss mice fasting for 17 h.

TABLE 4

Additive effect of compound 4 with metformin on glycaemia (mM/liter) in Swiss mice fasting for 17 h.

| Experimental conditions | Glycaemia Time (mn) | | | | | |
|---|---|---|---|---|---|---|
| | −60 | 0 | 30 | 60 | 90 | 120 |
| Carrier (n = 4) | 3.7 ± 0.2 | 4.5 ± 0.2 | 20.2 ± 2.6 | 18.0 ± 1.3 | 10.4 ± 0.2 | 7.8 ± 0.5 |
| Compound 4 (50 mg/kg) (n = 4) | 3.4 ± 0.2 | 4.0 ± 0.3 | 18.6 ± 3.2 | 13.3 ± 1.5 | 8.8 ± 1.0 | 6.8 ± 1.0 |
| Metformin (300 mg/kg) (n = 4) | 4.2 ± 0.3 | 3.6 ± 0.3 | 9.5 ± 0.6 | 11.2 ± 1.8 | 9.6 ± 0.9 | 8.6 ± 0.7 |
| Compound 4 (50 mg/kg) + Metformin (300 mg/kg) (n = 4) | 3.5 ± 0.3 | 3.3 ± 0.1 | 8.3 ± 1.2 | 5.5 ± 1.4 | 4.8 ± 1.1 | 4.5 ± 0.9 |

The 2 compounds were successively administered one hour before the glucose load. All the groups were composed of 4 mice (metformin alone, compound 4 alone, metformin+compound 4, control group with the carrier alone). Blood samples were taken at 0, 30, 60, 90 and 120 minutes after the glucose load.

After the glucose load, metformin alone caused the glycaemia area under curve to drop by 54.3%, compound 4 by 18.7% and the combination of metformin plus compound 4 by 76.4%. The effect is fully additive.

These results show a major effect of the compositions of the invention on changes in glycaemia levels.

EXAMPLE 4

Study on the Impact of Compound 2 on the Liver, Skeletal Muscle and Pancreas

A) On the Liver

Liver cells of rats fasting for 48 hours were incubated with lactate or glutamine in the absence and in the presence of 2 mM of compound 2. Enzymatic assay of the consumption of lactate and glutamine was performed, the production of their metabolites was also analysed. Finally the ATP cell concentration was determined.

The results are grouped together in Table 5 below.

TABLE 5

Effects of compound 2 (2 mM) on the metabolism of lactate and glutamine in liver cells of rats fasting for 48 h

| Experimental conditions | Consumption of substrate (—) | Glucose production | Complete oxidation | ATP concentration | NADH mitochondrial transport |
|---|---|---|---|---|---|
| 5 mM lactate | −4.49 ± 0.31 | 2.00 ± 0.13 | 0.04 ± 0.26 | 59.2 ± 12.0 | 0.48 ± 0.25 |
| 5 mM lactate + 2 mM compound 2 | −2.59 ± 0.34* | 0.76 ± 0.13* | 0.64 ± 0.30* | 31.8 ± 8.0* | 1.06 ± 0.33* |
| 5 mM glutamine | −1.79 ± 0.23 | 1.13 ± 0.17 | −0.78 ± 0.42 | 70.8 ± 11.3 | — |
| 5 mM glutamine + 2 mM compound 2 | −2.77 ± 0.15* | 0.78 ± 0.09* | 0.59 ± 0.35* | 34.2 ± 7.6* | — |

*$p < 0.05$, Student's test for paired data;
mean ± S.E.M.;
n = 6;
μmoles/flask except for ATP (nanomoles per 2 precisely cut liver sections);
complete oxidation: for lactate = consumption of lactate − (2 * glucose + pyruvate + alanine products), for glutamine = consumption of glutamine − (2 * glucose + pyruvate + lactate + alanine + glutamate products);
mitochondrial transport of NADH such as indicated above.

The results show that compound 2 stimulates complete oxidation of lactate and glutamine without increasing the ATP cell level, but on the contrary decreases this level. This suggests that decoupling occurs between oxidation of the substrates (lactate and glutamine) which is increased and phosphorylation of ADP to ATP which is reduced, whereas these 2 processes are normally coupled, i.e. they normally evolve in the same direction. The fact that the oxidation of the substrates is increased i.e. the flow of electrons at the respiratory chain is increased, is also evidenced by an increase in the intramitochondrial transport of NADH; this transport is equal to the difference between the consumption of lactate (the consumption of one molecule of lactate produces one molecule of NADH) and twice the production of glucose (since the synthesis of one molecule of glucose requires 2 molecules of NADH).

Study on the Metabolism of Lactate

Having regard to the fact that a 2 mM concentration of compound 2 leads to strong inhibition of lactate consumption (Table 5), a lower concentration of compound 2 (0.5 mM) was used to demonstrate an increase in complete oxidation of these substrates (lactate and glutamine) by this compound. For this demonstration, the same concentration (5 mM) of 1-, 2- and 3-13C-lactate was used, and lactate consumption and 13CO2 production were measured using quantitative carbon-13 NMR. Complete oxidation of a substrate was measured by the lowest CO2 value produced from one of its carbons. As a result, this carbon is found in greater quantity in non-volatile products (other than CO2) formed during the metabolism of this substrate.

Table 6 below shows that the non-volatile products formed during metabolism of lactate are better detected when using 2-13C-lactate as substrate. Complete oxidation of lactate can therefore be determined by measuring the production of 13CO2 from 2-13C-lactate.

TABLE 6

Sum of labelling of non-volatile products from lactate metabolism in liver cells of rats fasting for 48 h

| Experimental conditions | 1-13C-lactate | 2-13C-lactate | 3-13C-lactate |
|---|---|---|---|
| 5 mM lactate | 2.28 ± 0.05+ | 6.97 ± 0.10 | 5.92 ± 0.14+ |
| 5 mM lactate + 0.5 mM compound 2 | 1.36 ± 0.09*+ | 4.94 ± 0.15* | 4.06 ± 0.15*+ |

*$p < 0.05$ (different from control [lactate alone]),
+$p < 0.05$ (different from 2-13C-lactate), Student's t test for paired data;
mean ± S.E.M.;
n = 3;
μmoles of carbon 13/flask.

Table 7 below shows that compound 2 stimulates the complete oxidation of lactate although it slightly reduces (by 10%) the consumption of this substrate; this effect is accompanied by a reduction in the cell concentration of ATP, this being an essential molecule for the synthesis of glucose from lactate. Decoupling of oxidative phosphorylation is thereby demonstrated.

TABLE 7

Effect of MTBL0036 (0.5 mM) on the production of 13CO2 and glucose from 2-13C-lactate (5 mM) and ATP cell concentration in the liver cells of rats fasting for 48 h

| Experimental conditions | Glucose production | 13CO2 production | ATP concentration |
|---|---|---|---|
| 5 mM 2-13C-lactate | 6.17 ± 0.15 | 5.18 ± 0.19 | 243.6 ± 37.4 |
| 5 mM 2-13C-lactate + 0.5 mM compound 2 | 4.69 ± 0.14* | 5.99 ± 0.09* | 188.4 ± 25.2* |

*$p < 0.05$ (different from control [lactate alone], Student's t test for paired data;
mean ± S.E.M.;
n = 4;
μmoles/flask except for ATP (nanomoles per 6 precisely cut liver section).

Differences Between the Mechanism of Action of Compound 2 and of Metformin:

It is to be recalled here that lactate is the main substrate of liver gluconeogenesis.

It has been well proven that metformin is a moderate inhibitor of complex 1 of the respiratory chain, which leads to activation of AMPK and the resulting metabolic effects, in particular inhibition of liver gluconeogenesis. In rat liver cells, contrary to compound 2, metformin reduces the production of 13CO2 from 2-13C-lactate and the synthesis of glucose. On the other hand, compound 2 is an activator of the respiratory chain subsequent to a moderate decoupling effect of oxidative phosphorylation. This compound therefore has the potential to correct the mitochondrial deficiency existing in Type 2 diabetes by increasing oxidation of the substrates and simultaneously reducing liver synthesis of glucose.

Study on Lactate Metabolism

Complete oxidation of glutamine can be examined by measuring the production of 13CO2 from 3-13C-glutamine (Biochem. J., 2004, 378, 485-495).

Table 8 below shows that compound 2 increases the production of 13CO2 from 3-13C-glutamine without increasing ATP cell concentration.

TABLE 8

Effect of compound 2 (0.5 mM) on glucose production, complete glutamine oxidation and ATP cell concentration in liver cells of rats fasting for 48 h

| Experimental conditions | Glucose production | Production of 13CO2 | ATP concentration |
|---|---|---|---|
| 5 mM 3-13C-glutamine | 6.01 ± 0.09 | 0.23 ± 0.40 | 356.1 ± 41.4 |
| 5 mM 3-13C-glutamine + 0.5 mM compound 2 | 6.05 ± 0.30 (NS) | 1.86 ± 0.28* | 362.9 ± 53.3 (NS) |

*$p < 0.5$ (different from control [glutamine alone]), ANOVA assay followed by Newman Keuls assay;
mean ± S.E.M.;
n = 4 experiments;
μmoles/flask except for ATP (nanomoles per 6 precisely cut liver sections).
NS = statistically non-significant.

B) On Skeletal Muscle and the Pancreas

Insulin secretion in 6 STZ-N0a rats was observed in relation to administration of compound 2 (200 mg/kg) before (time −60 min and −30 min) and after a glucose load (time 0 min). An increase in insulin secretion was noted solely when compound 2 caused an increases in the peripheral consumption of glucose by skeletal muscle (Tables 9 to 12 which give a mean of the results obtained). Tables 9 and 10 show that an increase in muscle consumption of glucose (decreased AUC) is accompanied by an increase in the level of circulating insulin. It is shown in Tables 11 and 12 that if there is no increase in muscle consumption of glucose, there is no increase in the level of circulating insulin.

Since the 2 occurrences are related, the conclusion can be drawn that the increase in glucose consumption by skeletal muscle is due to stimulation of insulin secretion of which the mechanism of action is well known.

TABLE 9

Effects of compound 2 (200 mg/kg) on glycaemia

| Experimental conditions | Glycaemia (mmol/l) Time (mn) | | | | | | |
|---|---|---|---|---|---|---|---|
| | −60 | 0 | 30 | 60 | 90 | 120 | AUC |
| control (n = 6) | 4.62 | 4.83 | 11.63 | 17.38 | 16.33 | 12.98 | 1048 |
| Compound 2 (200 mg/kg) (n = 6) | 4.75 | 8.75 | 12.97 | 13.15 | 11.37 | 10.13 | 356 |

TABLE 10

Effects of compound 2 (200 mg/kg) on the concentration of circulating insulin in rats

| Experimental conditions | Insulin (ng/ml) Time (mn) | | | | | |
|---|---|---|---|---|---|---|
| | −60 | 0 | 30 | 60 | 90 | 120 |
| control (n = 6) | 0.47 | 0.41 | 0.70 | 0.59 | 0.54 | 0.53 |
| Compound 2 (200 mg/kg) (n = 6) | 0.47 | 0.41 | 0.70 | 0.59 | 0.54 | 0.53 |

TABLE 11

Effects of compound 2 (25 mg/kg) on glycaemia

| Experimental conditions | Glycaemia (mmol/l) Time (mn) | | | | | | |
|---|---|---|---|---|---|---|---|
| | −60 | 0 | 30 | 60 | 90 | 120 | AUC |
| control (n = 6) | 5.12 | 5.14 | 15.52 | 15.03 | 15.27 | 13.53 | 1025 |
| Compound 2 (200 mg/kg) (n = 6) | 5.12 | 5.23 | 11.15 | 16.21 | 14.36 | 15.33 | 1048 |

TABLE 12

Effects of compound 2 (25 mg/kg) on the concentration of circulating insulin in rats

| Experimental conditions | Insulin (ng/ml) Time (mn) | | | | | |
|---|---|---|---|---|---|---|
| | −60 | 0 | 30 | 60 | 90 | 120 |
| control (n = 6) | 1.5 | 1.16 | 2.17 | 1.79 | 1.34 | 1.33 |
| Compound 2 (200 mg/kg) (n = 6) | 1.11 | 1.41 | 1.76 | 1.48 | 1.61 | 1.61 |

Differences Between the Mechanism of Action of Compound 2 and of Metformin:

It has been well proven that at the skeletal muscle metformin acts via activation of AMPK.

Compound 2 acts differently at the skeletal muscle. It acts via insulin, the secretion of which is stimulated.

The invention claimed is:

1. A composition comprising metformin or a salt of metformin, a pharmaceutically acceptable carrier or excipient and at least one formula (I) compound and the enantiomers, diastereoisomers or pharmaceutically acceptable salts thereof:

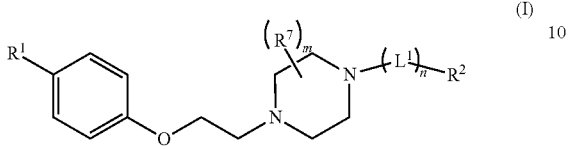

where:
R$^1$ is a group from among:
—C(O)CR$^3$R$^4$CR$^5$R$^6$C(O)OH;
—C(OH)(H)CR$^3$R$^4$CR$^5$R$^6$C(O)OH;
—(CH$_2$)$_4$C(O)OH; or

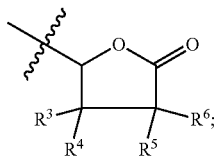

m is an integer ranging from 0 to 8;
n is 0 or 1;
L$^1$ is a group from among —C(O)—; —C(O)O— or —S(O)$_2$—;
R$^2$ is:
  a carbocycle group, 5-, 6 or 7-membered, saturated, partly unsaturated or aromatic, substituted or unsubstituted;
  a polycarbocycle group, 8- to 14-membered, saturated, partly unsaturated or aromatic, substituted or unsubstituted;
  a heterocycle group, 5-, 6- or 7-membered, substituted or unsubstituted, saturated, partly unsaturated or aromatic, optionally having 1, 2 or 3 heteroatoms, the same or different, selected from the group consisting of nitrogen, oxygen and sulfur;
  a polyheterocycle group, 8- to 14-membered, substituted or unsubstituted, saturated, partly unsaturated or aromatic, optionally having 1, 2 or 3 heteroatoms, the same or different, selected from the group consisting of nitrogen, oxygen and sulfur;
  -L$^2$-carbocycle group, the carbocycle being 5-, 6- or 7-membered, saturated, partly unsaturated or aromatic, substituted or unsubstituted;
  -L$^2$-polycarbocycle group, the polycarbocycle being 8- to 14-membered, saturated, partly unsaturated or aromatic, substituted or unsubstituted;
  -L$^2$-heterocycle group, the heterocycle being 5-, 6- or 7-membered, substituted or unsubstituted, saturated, partly unsaturated or aromatic and optionally having 1, 2 or 3 heteroatoms, the same or different, selected from the group consisting of nitrogen, oxygen and sulfur;
  -L$^2$-polyheterocycle group, the polyheterocycle being 8- to 14-membered, substituted or unsubstituted, saturate, partly unsaturated or aromatic, and optionally having 1, 2 or 3 heteroatoms, the same or different, selected from the group consisting of nitrogen, oxygen and sulfur; or
  hydrocarbon group, straight-chain or branched, C$_1$ to C$_5$;
L$^2$ being an alkyl, straight-chain or branched, C$_1$ to C$_5$;
R$^3$, R$^4$, R$^5$ and R$^6$, the same or different, are:
  a hydrogen atom;
  an alkyl group, straight-chain or branched, C$_1$ to C$_5$;
  a carbocycle group, 5-, 6- or 7-membered, saturated, partly unsaturated or aromatic, substituted or unsubstituted; or
  R$_3$ and R$_4$, together with the carbon atom to which they are attached, form a 5-, 6- or 7-membered carbocycle, substituted or unsubstituted, optionally saturated; or
  R$_5$ and R$_6$, together with the carbon atom to which they are attached, form a 5-, 6- or 7-membered carbocycle, substituted or unsubstituted, optionally saturated;
R$^7$, the same or different, are:
  an alkyl, straight-chain or branched, C$_1$ to C$_5$;
  -L$^2$-carbocycle group, the carbocycle being 5-, 6- or 7-membered, saturated, partly unsaturated or aromatic, substituted or unsubstituted;
  -L$^2$-polycarbocycle group, the polycarbocycle being 8- to 14-membered, saturated, partly unsaturated or aromatic, substituted or unsubstituted;
  -L$^2$-heterocycle group, the heterocycle being 5-, 6- or 7-membered, substituted or unsubstituted, saturated, partly unsaturated or aromatic and optionally having 1, 2 or 3 heteroatoms, the same or different, selected from the group consisting of nitrogen, oxygen and sulfur; or
  -L$^2$-polyheterocycle group, the polyheterocycle being 8- to 14-membered, substituted or unsubstituted, saturated, partly unsaturated or aromatic and optionally having 1, 2 or 3 heteroatoms, the same or different, selected from the group consisting of nitrogen, oxygen and sulfur.

2. The composition according to claim 1 wherein R$^7$, the same or different, are:
  an alkyl, straight-chain or branched, C$_1$ to C$_3$; or
  -L$^2$-carbocycle group, L$^2$ representing an alkyl, straight-chain or branched, C$_1$ to C$_5$; and the carbocycle being aromatic with 5 or 6 members, optionally substituted.

3. The composition according to claim 1 wherein m is 0 or 1.

4. The composition according to claim 1 wherein R$^2$ is:
  a 6-membered aromatic carbocycle group, unsubstituted or substituted by one or more substituents, the same or different, selected from the group consisting of:
    C$_1$ to C$_6$ alkoxy group, straight-chain or branched;
    a halogen atom;
    C$_1$ to C$_5$ alkyl group, straight-chain or branched; and
    C$_1$ to C$_5$ alkyl group, straight-chain or branched, substituted by one or more halogen atoms;
  5- or 6-membered heterocycle group having 1, 2 or 3 heteroatoms, the same or different, selected from group consisting of nitrogen, sulfur and oxygen, unsubstituted or substituted by one or more substituents, the same or different selected from the group consisting of:
    C$_1$ to C$_6$ alkoxy group, straight-chain or branched;
    a halogen atom;
    C$_1$ to C$_5$ alkyl group, straight-chain or branched;
    C$_1$ to C$_5$ alkyl group, straight-chain or branched, substituted by one or more halogen atoms.

5. The composition according to claim 1 wherein n is 0.

6. The composition according to claim 1 wherein R$^3$, R$^4$, R$^5$ and R$^6$, the same or different, represent:

a hydrogen atom;
an alkyl group, straight-chain or branched, $C_1$ to $C_5$;
a carbocycle, 5-, 6- or 7-membered, saturated, partly unsaturated or aromatic, substituted or unsubstituted; or
$R^3$ and $R^4$, together with the carbon atom to which they are attached, form a 5-, 6- or 7-membered carbocycle, substituted or unsubstituted, optionally saturated; or
$R^5$ and $R^6$, together with the carbon atom to which they are attached, form a 5-, 6- or 7-membered carbocycle, substituted or unsubstituted, optionally saturated.

7. The composition according to claim 1 wherein $R^1$ is —C(O)CR$^3$R$^4$CR$^5$R$^6$C(O)OH or —(CH$_2$)$_4$C(O)OH.

8. The composition according to claim 1 wherein $R^3$, $R^4$, $R^5$ and $R^6$ each represent a hydrogen atom.

9. The composition according to claim 1 wherein the formula (I) compound is selected from the group consisting of:

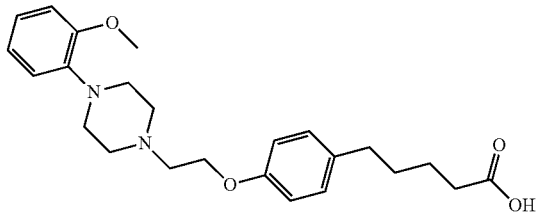

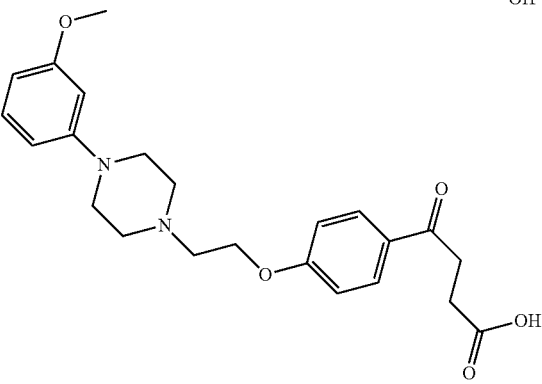

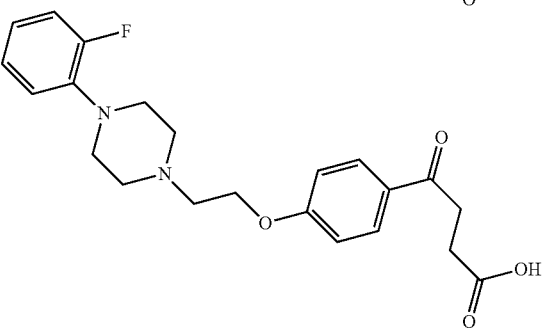

and

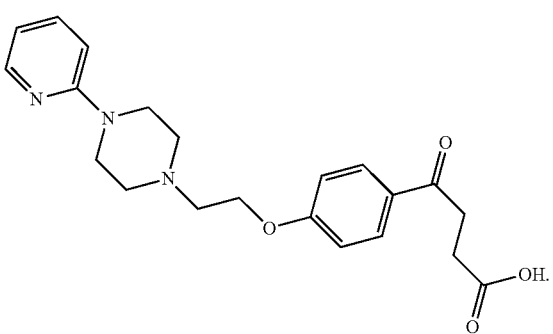

10. A kit comprising at least one formula (I) compound according to claim 1 or one of the pharmaceutically acceptable salts thereof, and metformin or a salt of metformin for simultaneous, separate or sequential administration to a patient in need thereof.

11. A method for selecting a compound for the treatment of pathologies associated with insulin-resistance syndrome, having an additional effect adding to the effect of metformin, comprising the steps of:
   a) providing fasting, normal animals;
   b) measuring glycaemia in these animals;
   c) administering the compound to be tested to one portion of the animals, metformin to a second portion of the animals and an association of metformin and the compound to be tested to the last portion of the animals;
   d) administering a glycose load to the animals comprising 2 to 4 g/kg animal body weight;
   e) measuring glycaemia at different times; and
   f) determining whether the compound has an additive effect to the effect of metformin on lowering of glycaemia, comprising comparing the glycaemia area under curve obtained for each of the compounds administered, and determining whether the tested compound in association with metformin allowed a reduction in the glycaemia area under curve compared with metformin administered alone.

12. The method according to claim 11 comprising a step g) to select the compound if it responds positively at step f).

13. The method according to claim 11 comprising, before step a), the prior steps of:
   1) determining the toxicity of the compound to be tested;
   2) providing liver cells of fasting animals;
   3) incubating these cells with lactate or glutamine;
   4) adding the compound to be tested to the incubation medium;
   5) performing enzymatic assay of lactate or glutamine consumption and/or of glucose production and/or assay of ATP cell concentration;
   6) determining those non-toxic or scarcely toxic compounds allowing stimulation of complete lactate or glutamine oxidation and/or a reduction in ATP cell concentration; and/or
   7) providing animals having Type 2 diabetes;
   8) administering the compound to be tested to these animals;
   9) administering a glucose load to the animals comprising 1 to 3 g/kg animal body weight;
   10) evaluating the peripheral consumption of glucose by skeletal muscle and/or the concentration of circulating insulin;
   11) determining those non-toxic or scarcely toxic compounds allowing an increase in the consumption of glucose by muscle and/or an increase in the concentration of circulating insulin, the implementation of steps a) to f) being performed either on the compounds responding positively at step 6) or on the compounds responding positively at step 11), or on the compounds responding positively at steps 6) and 11).

14. A method to select non-toxic or scarcely toxic compounds allowing the stimulation of complete lactate or glutamine oxidation and/or a reduction in ATP cell concentration, comprising the following steps:
   1) determining the toxicity of the compound to be tested;
   2) providing liver cells of fasting animals;
   3) incubating these cells with lactate or glutamine;
   4) adding the compound to be tested to the incubation medium;

5) performing enzymatic assay of the consumption of lactate or glutamine and/or of the production of glucose and/or assay of ATP cell concentration;
   6) determining those non-toxic or scarcely toxic compounds allowing stimulation of complete lactate or glutamine oxidation and/or a reduction in ATP cell concentration.

15. The method according to claim 14 comprising a step 7) to select the compound if it responds positively at step 6).

16. A method for producing a composition comprising adding to metformin, or a salt of metformin, at least one compound selected by the method according to claim 11.

17. A method for treating pathologies associated with insulin-resistance syndrome, comprising the administration of an efficient amount of a composition according to claim 1 to a patient in need thereof.

18. The method according to claim 17, for the treatment of diabetes.

19. The method according to claim 17 to inhibit neoglucogenesis.

20. The method according to claim 18, for the treatment of Type 2 diabetes.

* * * * *